United States Patent
Min et al.

(10) Patent No.: US 7,912,544 B1
(45) Date of Patent: Mar. 22, 2011

(54) CRT RESPONDER MODEL USING EGM INFORMATION

(75) Inventors: Xiaoyi Min, Thousand Oaks, CA (US); Josh Reiss, Kirkland, WA (US)

(73) Assignee: Pacesetter, Inc., Sylmar, CA (US)

( * ) Notice: Subject to any disclaimer, the term of this patent is extended or adjusted under 35 U.S.C. 154(b) by 957 days.

(21) Appl. No.: 11/738,426

(22) Filed: Apr. 20, 2007

(51) Int. Cl.
A61N 1/18 (2006.01)

(52) U.S. Cl. .......................... 607/9; 600/521

(58) Field of Classification Search ........ 607/9; 600/508, 600/509, 516, 521
See application file for complete search history.

(56) References Cited

U.S. PATENT DOCUMENTS

| | | | |
|---|---|---|---|
| 4,712,555 | A | 12/1987 | Thornander et al. |
| 4,788,980 | A | 12/1988 | Mann et al. |
| 4,928,688 | A | 5/1990 | Mower |
| 4,940,052 | A | 7/1990 | Mann et al. |
| 4,944,298 | A | 7/1990 | Sholder |
| 5,086,774 | A | 2/1992 | Duncan |
| 5,174,289 | A | 12/1992 | Cohen |
| 5,466,254 | A | 11/1995 | Helland |
| 5,476,483 | A | 12/1995 | Bornzin et al. |
| 5,643,327 | A | 7/1997 | Dawson et al. |
| 5,741,308 | A | 4/1998 | Sholder |
| 5,814,077 | A | 9/1998 | Sholder et al. |
| 5,873,895 | A | 2/1999 | Sholder et al. |
| 6,122,546 | A | 9/2000 | Sholder et al. |
| 6,144,880 | A | 11/2000 | Ding et al. |
| 6,285,907 | B1 | 9/2001 | Kramer et al. |
| 6,314,323 | B1 | 11/2001 | Ekwall |
| 6,360,127 | B1 | 3/2002 | Ding et al. |
| 6,411,848 | B2 | 6/2002 | Kramer et al. |
| 6,424,865 | B1 | 7/2002 | Ding |
| 6,567,700 | B1 | 5/2003 | Turcott et al. |
| 6,622,040 | B2 | 9/2003 | Ding et al. |
| 6,668,194 | B2 | 12/2003 | VanHout |
| 6,804,555 | B2 | 10/2004 | Warkentin |
| 6,934,586 | B2 | 8/2005 | Struble et al. |
| 6,959,214 | B2 | 10/2005 | Pape et al. |
| 7,283,864 | B2 * | 10/2007 | Thomas et al. ............. 600/516 |
| 2001/0016759 | A1 | 8/2001 | Kramer et al. |
| 2001/0031993 | A1 | 10/2001 | Salo et al. |
| 2002/0049478 | A1 | 4/2002 | Ding et al. |
| 2002/0062139 | A1 | 5/2002 | Ding |
| 2002/0077559 | A1 | 6/2002 | Ding et al. |

(Continued)

FOREIGN PATENT DOCUMENTS

EP 1199085 A2 4/2002

(Continued)

OTHER PUBLICATIONS

Gerber, Thomas C. et al., "Left Ventricular and Biventricular Pacing in Congestive Heart Failure," Mayo Clin Proc 2001; 76:803-812.

(Continued)

Primary Examiner — Eric D. Bertram

(57) ABSTRACT

An exemplary method includes detecting a QRS complex using cutaneous electrodes, during the QRS complex, detecting an R-wave of a ventricle using an intracardiac electrode, determining if the R-wave occurred during a first, predetermined percentage of the QRS complex width and, based at least in part on the determining, deciding whether a patient is likely to respond to cardiac resynchronization therapy. Such a method may set the predetermined percentage to approximately 50%. An exemplary model includes a parameter for a percentage for the timing of an EGM R-wave with respect to the total width of an ECG QRS complex. Various other exemplary methods, devices, systems, etc. are also disclosed.

11 Claims, 24 Drawing Sheets

U.S. PATENT DOCUMENTS

| | | |
|---|---|---|
| 2002/0161410 A1 | 10/2002 | Kramer et al. |
| 2003/0014084 A1 | 1/2003 | VanHout |
| 2003/0060851 A1 | 3/2003 | Kramer et al. |
| 2003/0130702 A1 | 7/2003 | Kramer et al. |
| 2003/0204212 A1 | 10/2003 | Burnes et al. |
| 2004/0133246 A1 | 7/2004 | Ding et al. |
| 2004/0147966 A1 | 7/2004 | Ding et al. |
| 2004/0193223 A1 | 9/2004 | Kramer et al. |
| 2006/0178586 A1* | 8/2006 | Dobak, III .................... 600/508 |

FOREIGN PATENT DOCUMENTS

| | | |
|---|---|---|
| EP | 1234597 A2 | 8/2002 |
| WO | 9958191 | 11/1999 |
| WO | 03037427 A1 | 5/2003 |

OTHER PUBLICATIONS

Merino, Jose L. MD et al., "Bundle-Branch Reentry and the Postpacing Interval After Entrainment by Right Ventricular Apex Stimulation—A New Approach to Elucidate the Mechanism of Wide-QRS-Complex Tachycardia With Atrioventricular Dissociation," Circulation 2001; 103:1102-1108.

Nelson, Gregory S. PhD et al., "Left Ventricular or Biventricular Pacing Improves Cardiac Function at Diminished Energy Cost in Patients With Dilated Cardiomyopathy and Left Bundle-Branch Block," Circulation 2000; 102:3053-3059.

Wang, Paul et al., "Timing Cycles for Biventricular Pacing," PACE 2002; 25:62-75.

Schuchert, Andreas et al., "Effects of Body Position and Exercise on Evoked Response Signal for Automatic Threshold Activation," PACE 1999; 22:1476-1480.

* cited by examiner

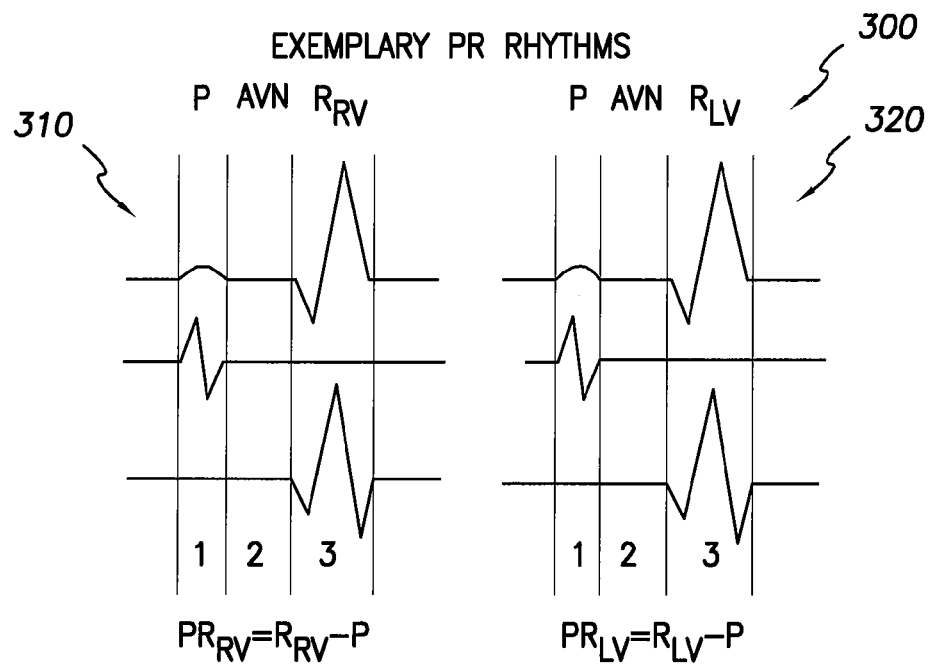
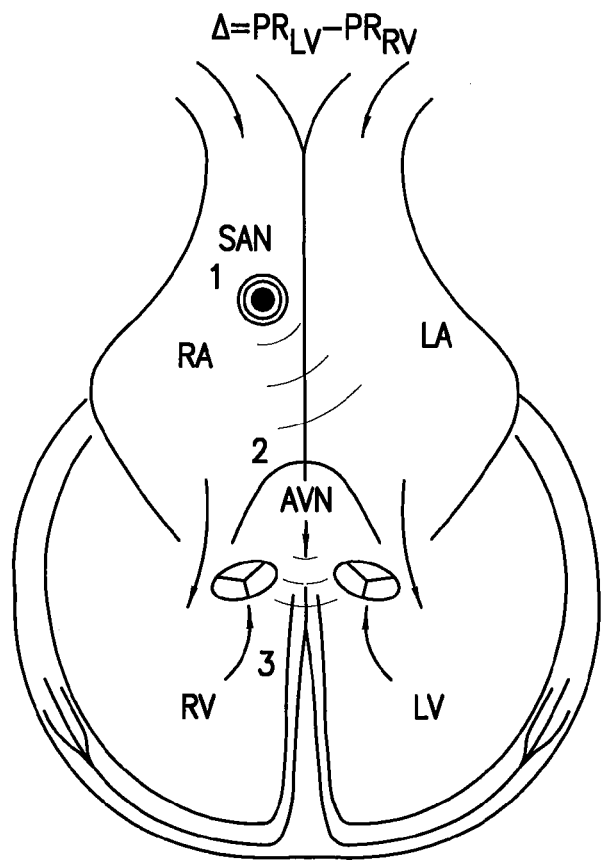
FIG. 3

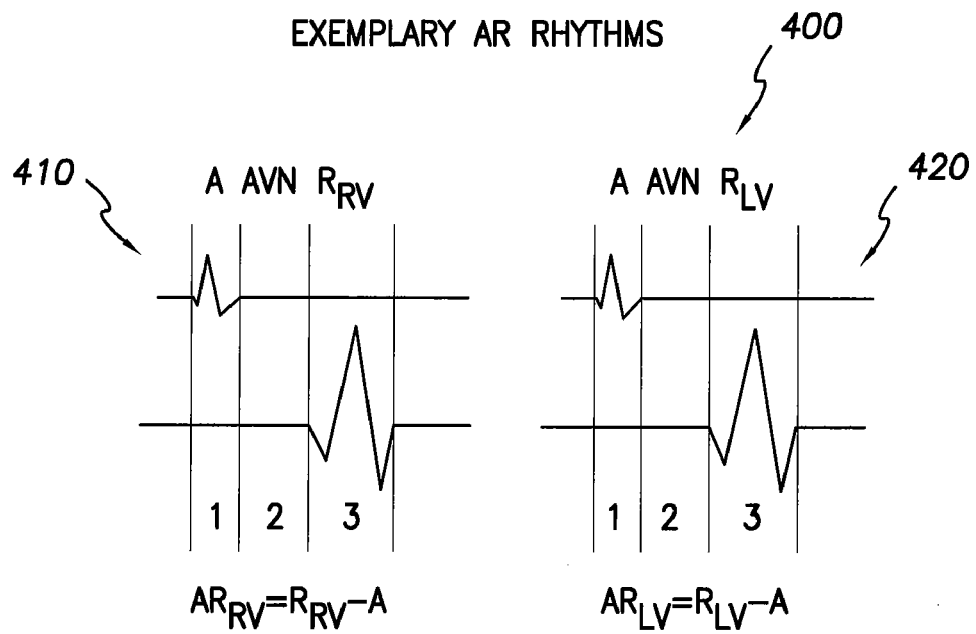
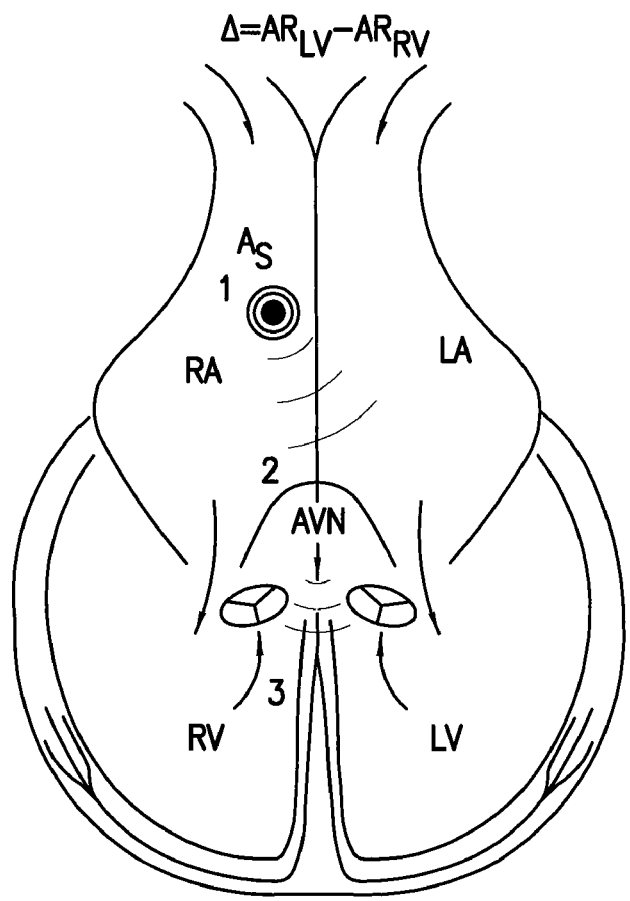
FIG. 4

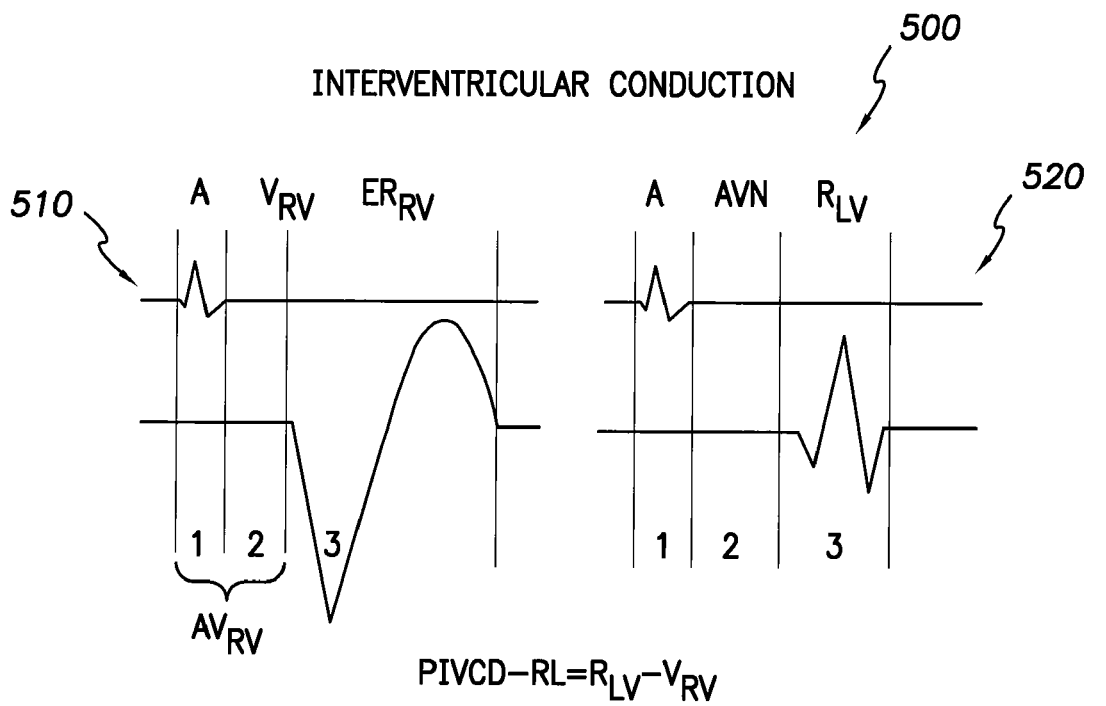
$$\Delta_{PIVCD} = (R_{RV} - V_{LV}) - (R_{LV} - V_{RV})$$
$$PIVCD-RL = R_{LV} - V_{RV}$$
$$\Delta_{PIVCD} = PIVCD-LR - PIVCD-RL$$
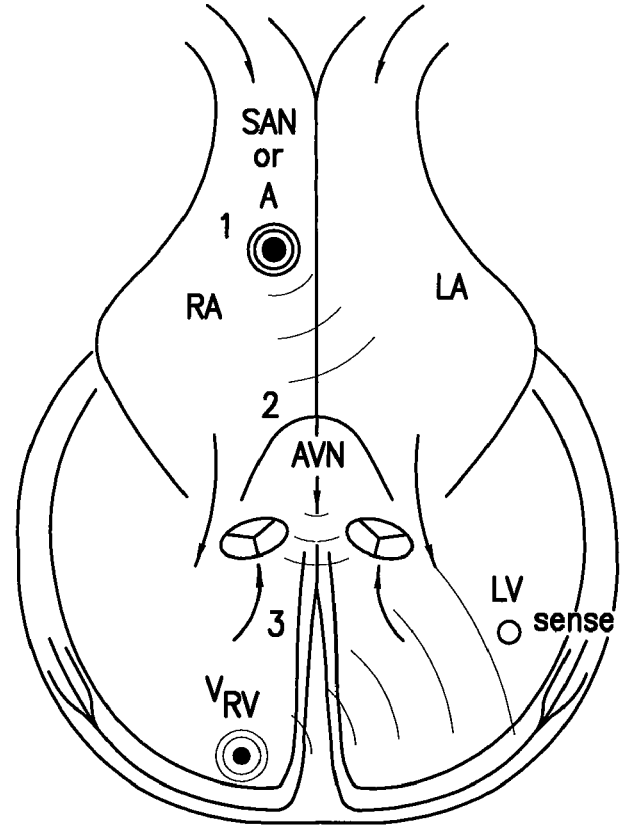
FIG. 5

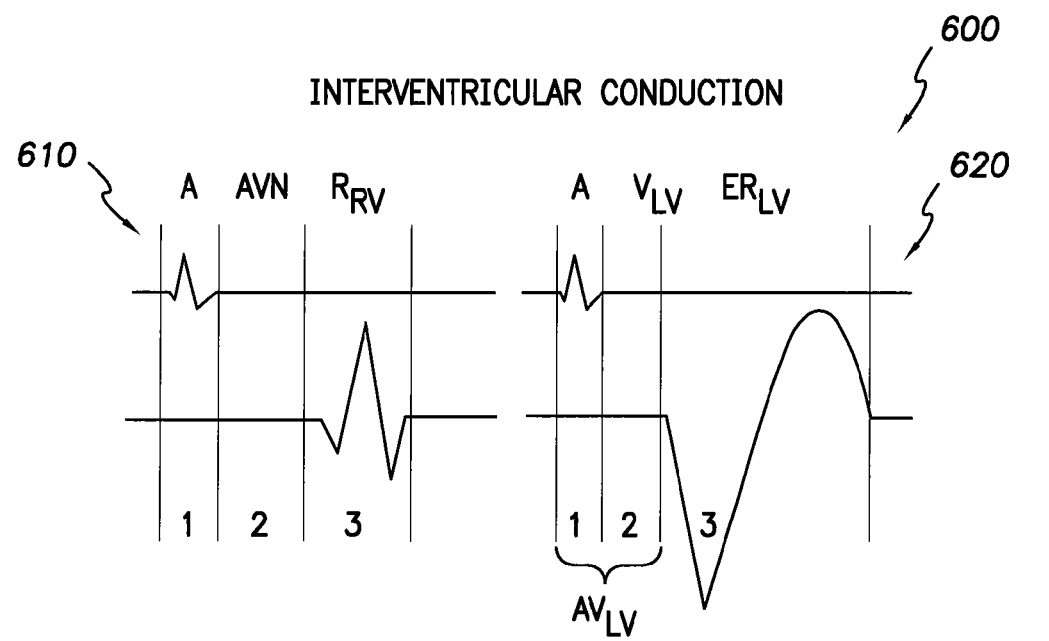
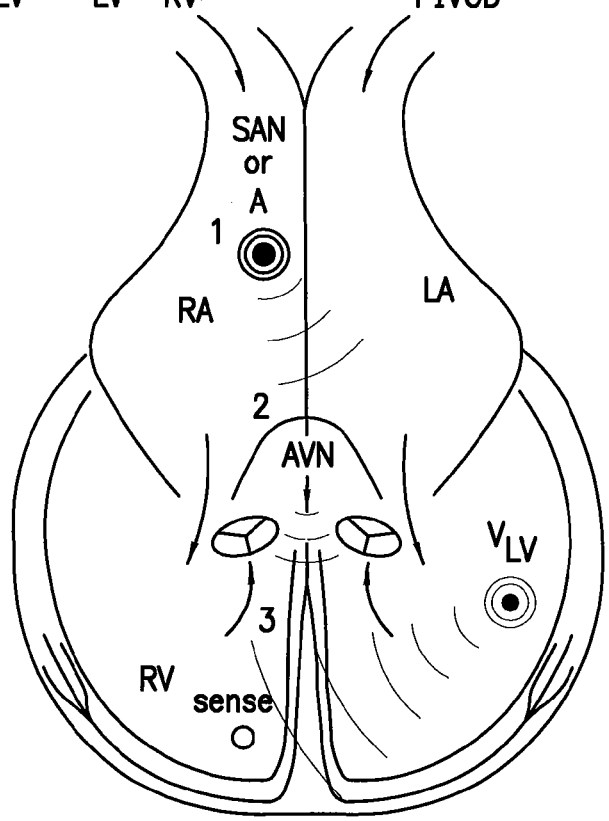
FIG. 6

FIG. 11

- 1102 IMPLANT RV LEAD AND PLACE LV LEAD AT POTENTIAL SITE
- 1104 DETERMINE DELAY BETWEEN ACTIVITY SENSED BY RV AND LV LEADS (OPTIONALLY DETERMINE ORDER OF INTRINSIC ACTIVITY)
- 1106 DOES DELAY EXCEED A PRESET THRESHOLD ?
  - Y → 1108 PLACEMENT OF LEADS IS SUITABLE
  - N → 1110 PACE LATER-ACTIVATING VENTRICLE AND SENSE ACTIVATION IN OTHER VENTRICLE; DETERMINE IVCD
- 1112 DOES IVCD EXCEED A PRESET THRESHOLD ?
  - N → 1114 MOVE LV LEAD TO NEW LOCATION
  - (Y) → 1108 PLACEMENT OF LEADS IS SUITABLE

1100

EXEMPLARY SEVEN LEAD ARRANGEMENT
1500
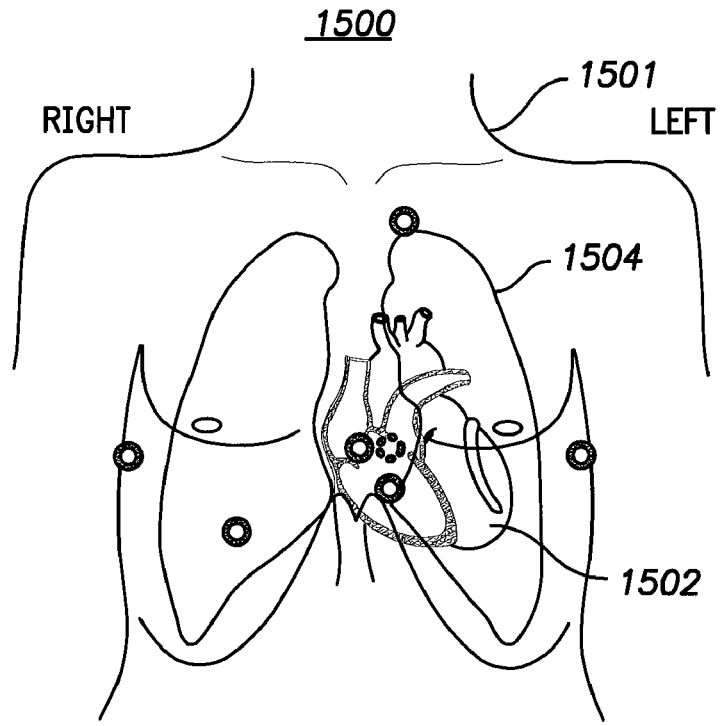
EXEMPLARY COORDINATE SYSTEM 1540
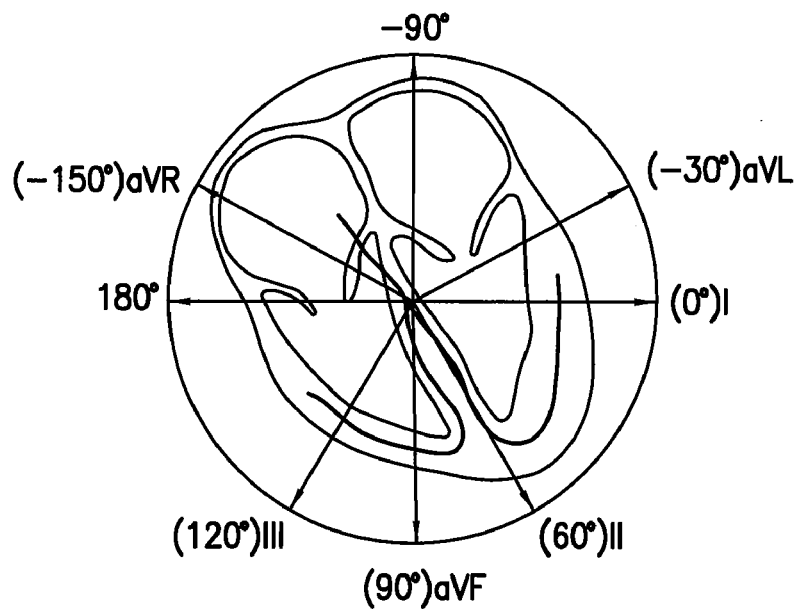
FIG. 15

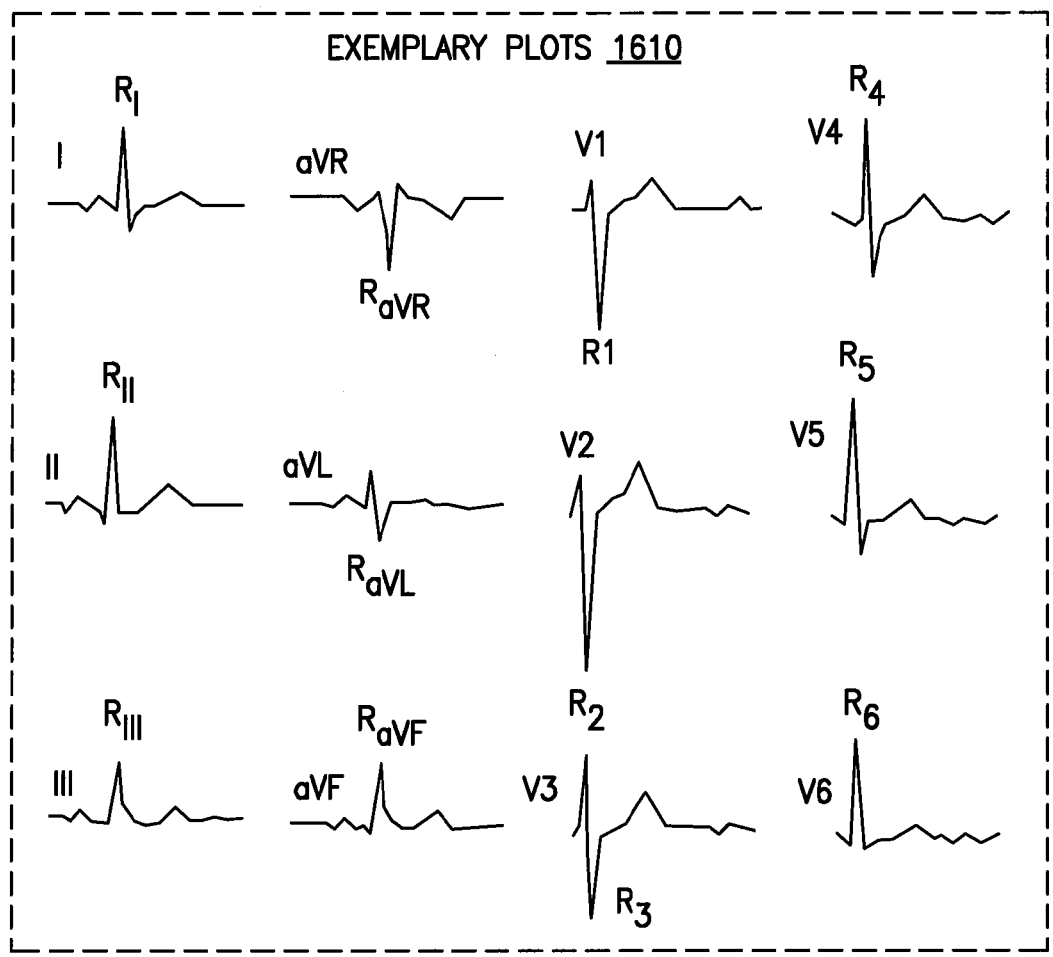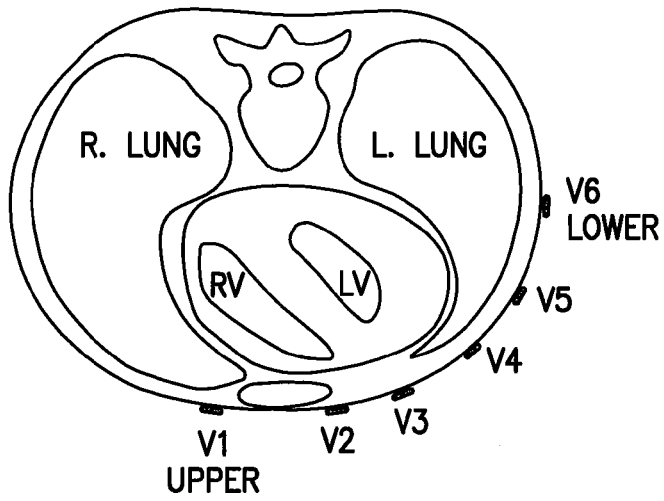
FIG. 16

RV DATA 2010

| ECG SITE | EGM SITE | % |
|---|---|---|
| I | RV$_{TIP-RING}$ | |
| II | RV$_{TIP-RING}$ | |
| III | RV$_{TIP-RING}$ | |
| aVr | RV$_{TIP-RING}$ | |
| aVL | RV$_{TIP-RING}$ | |
| aVF | RV$_{TIP-RING}$ | |
| V1 | RV$_{TIP-RING}$ | |
| V2 | RV$_{TIP-RING}$ | |
| V3 | RV$_{TIP-RING}$ | |
| V4 | RV$_{TIP-RING}$ | |
| V5 | RV$_{TIP-RING}$ | |
| V6 | RV$_{TIP-RING}$ | |

LV DATA 2020

| ECG SITE | EGM SITE | % |
|---|---|---|
| I | LV$_{COIL-RING-1}$ | |
| II | LV$_{COIL-RING-1}$ | |
| III | LV$_{COIL-RING-1}$ | |
| aVR | LV$_{TIP-RING-2}$ | |
| aVL | LV$_{TIP-RING-2}$ | |
| aVF | LV$_{TIP-RING-2}$ | |
| V1 | LV$_{TIP-RING-1}$ | |
| V2 | LV$_{TIP-RING-1}$ | |
| V3 | LV$_{TIP-RING-1}$ | |
| V4 | LV$_{TIP-RING-1}$ | |
| V5 | LV$_{TIP-RING-1}$ | |
| V6 | LV$_{TIP-RING-1}$ | |

FIG. 20

CRT RESPONDER MODEL USING EGM INFORMATION

CROSS-REFERENCE TO RELATED APPLICATIONS

This application is related to the following copending U.S. Patent Applications: 1) Ser. No. 11/129,540, filed May 13, 2005, titled "System and Method for Improving CRT Response and Identifying Potential Non-Responders to CRT Therapy"; and 2) U.S. patent application Ser. No. 10/703,070, filed Nov. 5, 2003, titled "Methods for Ventricular Pacing." The aforementioned patent applications are incorporated by reference herein.

TECHNICAL FIELD

Subject matter presented herein pertains generally to cardiac pacing and/or stimulation therapy. More specifically, various exemplary technologies pertain to capture detection, especially where bi-ventricular pacing may be used.

BACKGROUND

Heart failure affects millions of people worldwide. Heart failure often manifests itself in relatively wide QRS signals, signifying a desynchronization between electrical activation of the right and left ventricles. Often, a left bundle branch block (LBBB) interrupts the normal conduction path to the left ventricle and results in the intrinsic conduction taking a relatively long time to reach the left ventricle, causing it to be activated well after the right ventricle. This abnormal conduction delay results in a very inefficient contraction, which, in turn, produces low cardiac output. With low cardiac output, patients are unable to be very active. Over time, heart failure progressively worsens as does quality of life.

While various drug therapies may help some patients with bundle branch block, electrical cardiac stimulation often proves to be more effective than drug therapy alone, especially for patients that meet certain criteria. Such electrical cardiac stimulation is referred to as cardiac resynchronization therapy (CRT), which typically involves delivering electrical stimulation to the left ventricle (e.g., for LBBB) to compensate for delay conduction of intrinsic activity to the left ventricle. With appropriate timing, CRT increases cardiac output and improves quality of life.

While CRT is often beneficial, some questions remain regarding the optimal selection criteria for prescribing CRT. For patients who meet conventional CRT implant criteria, a relatively large percentage (about 30%) of those patients do not respond to CRT therapy. Hence, a need exists for technologies to increase the likelihood that a patient will respond favorably to CRT. Various technologies discussed herein aim to meet this need and/or other needs related to cardiac condition.

SUMMARY

An exemplary method includes detecting a QRS complex using cutaneous electrodes, during the QRS complex, detecting an R-wave of a ventricle using an intracardiac electrode, determining if the R-wave occurred during a first, predetermined percentage of the QRS complex width and, based at least in part on the determining, deciding whether a patient is likely to respond to cardiac resynchronization therapy. Such a method may set the predetermined percentage to approximately 50%. An exemplary model includes a parameter for a percentage for the timing of an EGM R-wave with respect to the total width of an ECG QRS complex. Various other exemplary methods, devices, systems, etc. are also disclosed.

BRIEF DESCRIPTION OF THE DRAWINGS

Features and advantages of the described implementations can be more readily understood by reference to the following description taken in conjunction with the accompanying drawings.

FIG. 3 is an approximate anatomical diagram of a heart, a surface ECG and two IEGM waveforms that exhibit an intrinsic P wave and an R wave.

FIG. 4 is an approximate anatomical diagram of a heart and two IEGM waveforms that exhibit an A wave and an R wave.

FIG. 5 is an approximate anatomical diagram of a heart and two sets of IEGM waveforms wherein one set includes an evoked response in a right ventricle and the other set includes a response from a conducted event in a left ventricle.

FIG. 6 is an approximate anatomical diagram of a heart and two sets of IEGM waveforms wherein one set includes an evoked response in a left ventricle and the other set includes a response from a conducted event in a right ventricle.

FIG. 11 is a flow chart of another exemplary method for determining whether electrode placement is suitable for CRT therapy

FIG. 15 is a diagram of a 7-lead arrangement for acquiring ECGs and a diagram of the heart and associated electrical activity vectors.

FIG. 16 is a series of ECG plots from a 12-lead arrangement and a diagram of the thorax identifying approximate locations for electrodes V1-V6.

FIG. 20 is a series of data tables that identify a surface ECG electrode configuration and an EGM electrode configuration for each ventricle.

DETAILED DESCRIPTION

The following description includes the best mode presently contemplated for practicing the described implementations. This description is not to be taken in a limiting sense, but rather is made merely for the purpose of describing the general principles of the implementations. The scope of the invention should be ascertained with reference to the issued claims. In the description that follows, like numerals or reference designators are used at times to reference like parts or elements throughout the description.

Overview

Exemplary methods, devices, systems, etc., pertain generally to acquiring EGM information and optionally ECG information to decide if a patient is a responder, for example, given a particular arrangement of leads, electrodes, etc., in the patient's body. Various techniques use an exemplary model to score a patient, optionally accounting for arrangement of leads, electrodes, etc. Such a model uses a variety of measures to determine a score value where the score value may be compared to past scores for the patient, scores from other patients, one or more theoretical score values, etc. Individual measures may also be compared to past measures for the patient, measures from other patients, one or more theoretical measures, etc. Such a comparison or comparisons may help guide a clinician as to treatment options.

At time of implant of a cardiac therapy device, an exemplary method may help a clinician assess various arrangements of leads, electrodes, etc. After implantation, an exemplary method may help a clinician assess a patient's progress and optionally adjust electrode configuration. Where appropriately configured, an exemplary device may perform such an assessment and/or an adjustment to electrode configuration. For example, where the assessment indicates that a patient's responder score is sub-optimal, then an implantable device may call for an adjustment to an electrode configuration to achieve a better responder score.

The following description begins with a discussion of exemplary implantable devices and associated components followed by a discussion of heart rhythms and associated waveforms. Next, a discussion of cardiac performance follows, and the detailed description continues with a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
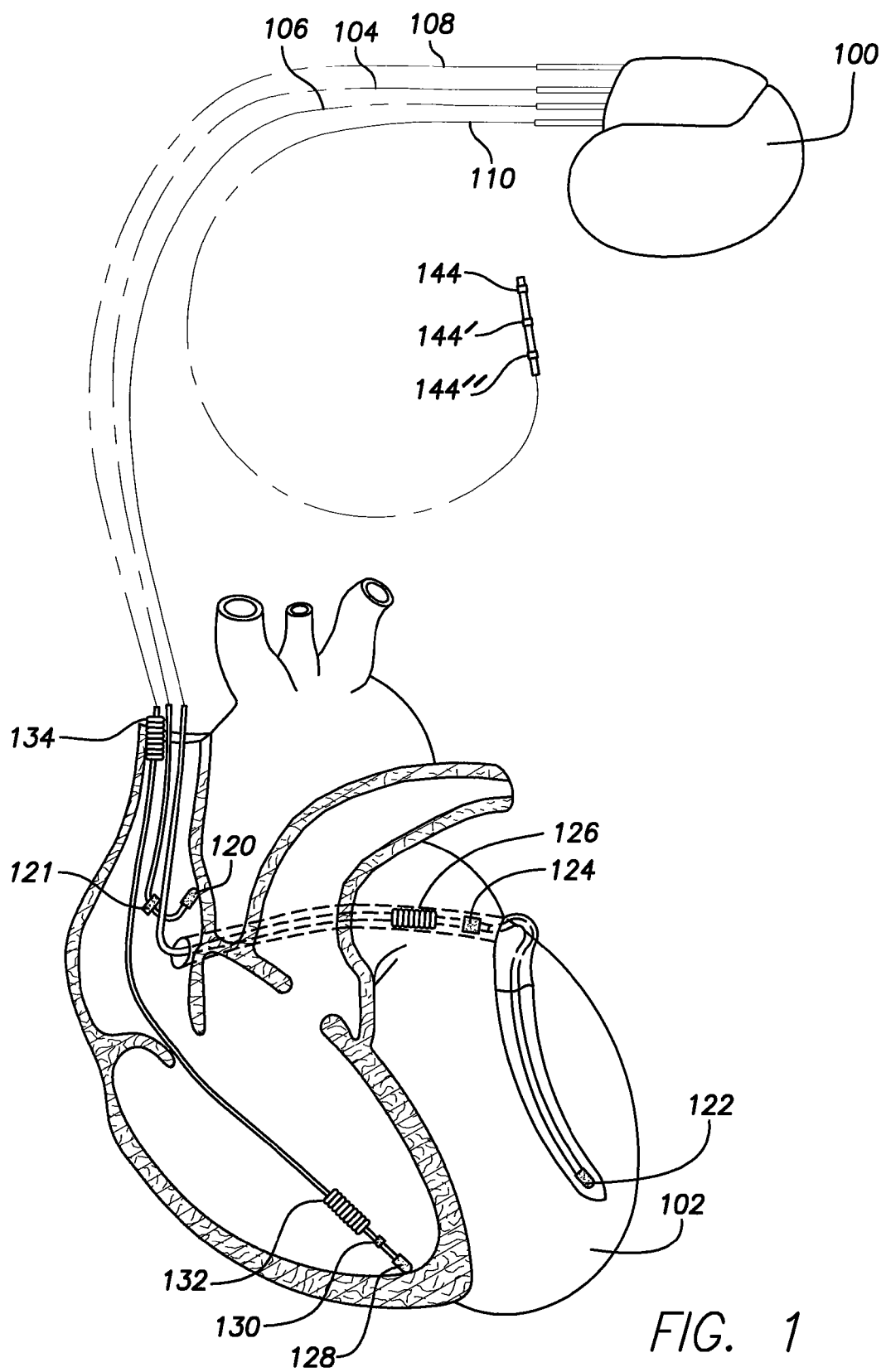
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 may optionally include a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein. As will be described in greater detail below, the illustrative method tests one or more placement locations of the coronary sinus lead 106 to determine a suitable placement for lead 106.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
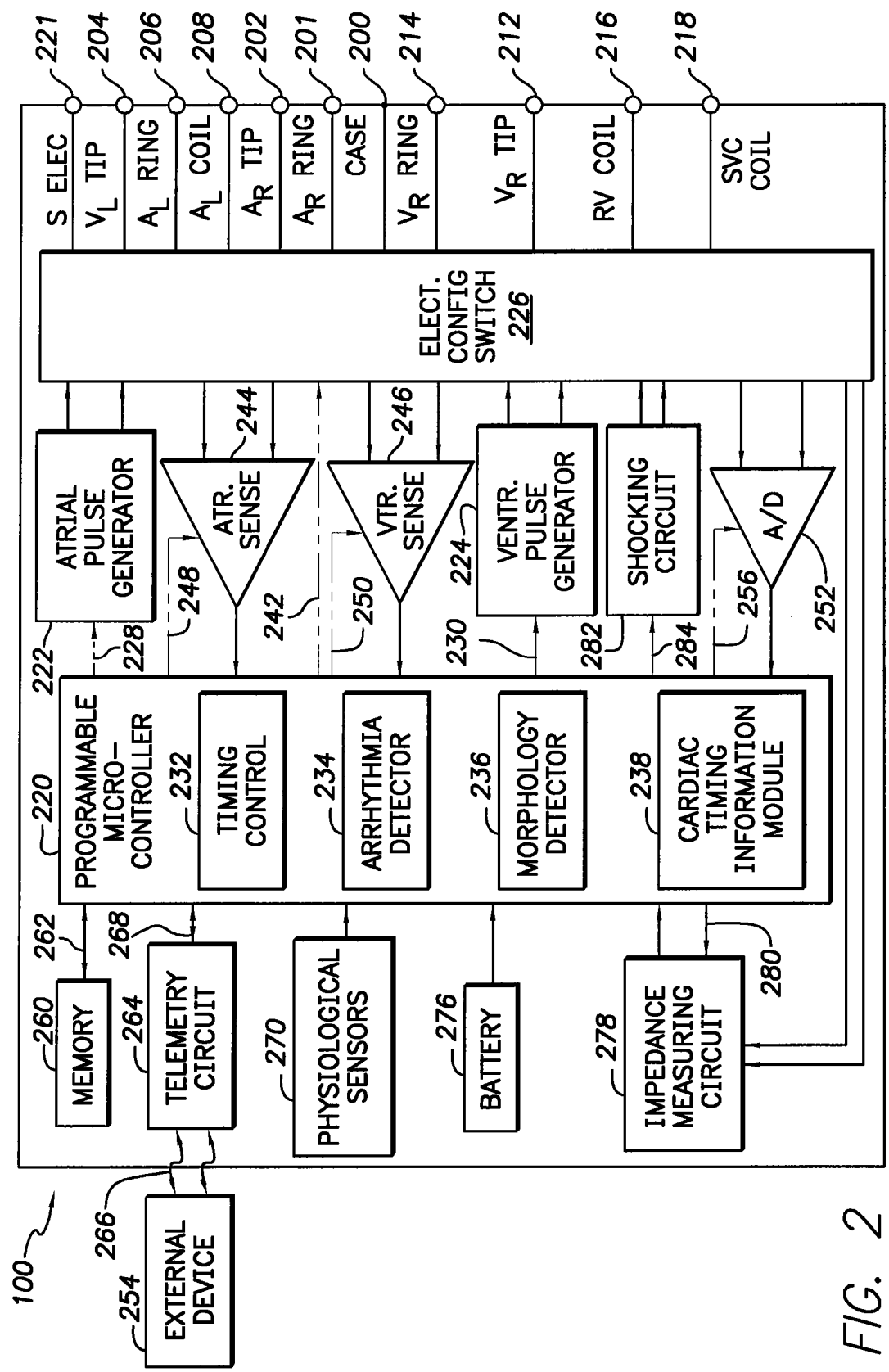
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a cardiac timing information module 238 for determining a selected cardiac timing parameter. As described above, in one embodiment module 238 determines an intrinsic conduction delay between right ventricular activation and left ventricular activation. In other embodiments, module 238 determines an interval between stimulation of one ventricle and sensing of propagated electrical activity to the other ventricle. Module 238 may be implemented in hardware as part of the microcontroller 220, or as software/firmware instructions programmed into the device and executed on the microcontroller 220 during certain modes of operation. The module 238 may be capable of implementing various exemplary methods (see, e.g., the device 100 of FIG. 24).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. The microcontroller 220 may control the A/D system 252 via a control line 256, for example, to select a resolution, a gain, a ground, etc., which may occur in conjunction with one or more other instructions (e.g., an instruction to the switch 226, etc.).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction.) The embodiments described herein use the $\Delta$ value to determine whether the current lead positioning is adequate, or whether it needs to be changed.

The variable $\Delta$ represents an interventricular delay that is based on an atrio-ventricular delay for the left ventricle ($PR_{LV}$) and an atrio-ventricular delay for the right ventricle ($PR_{RV}$). The variable $|\Delta|$ is shown as the absolute value of the difference while herein and in the figures the variable $\Delta$ (e.g, $\Delta=PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa. In general, the acronym IVCD (e.g., IVCD, IVCD-RL, IVCD-LR or $\Delta_{IVCD}$) may refer to one or more types of interventricular conduction delays, whether paced ventricular, paced atrial, or intrinsic. An interventricular conduction delay, regardless of type, pertains to direction of a wavefront, i.e., from left ventricle to right ventricle or from right ventricle to left ventricle. An IVCD depends on a position of an electrode and/or electrode configuration.

With respect to cardiac condition, a long interventricular delay may be indicative of a conduction block. For example, left bundle branch block (LBBB) may cause the left ventricle to contract more than approximately 50 ms after contraction of the right ventricle (e.g., $\Delta>0$). Whereas a right bundle branch block (RBBB) may be expected to cause the right ventricle to contract well after the left ventricle (e.g., $\Delta<0$). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

FIG. 4 shows an approximate anatomical diagram of a heart and two sets of waveforms 400. One set of waveforms 410 corresponds in part to right ventricular activity while another set of waveforms 420 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 410, 420 show various IEGMs of heart activity (e.g., polarization, depolarization, etc.) wherein atrial depolarization is represented as an "A wave" and ventricular depolarization is represented as an "R wave", or QRS complex. Both sets 410, 420 show an A wave followed by an AVN conduction delay (AVN) and a right ventricular R wave or QRS complex ($R_{RV}$) for the set 410 and a left ventricular R wave or QRS complex ($R_{LV}$) for the set 420. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 4 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g, $\Delta=AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode, etc.

FIGS. 5 and 6 show plots, approximate anatomical diagrams and equations associated with yet another delay time, $\Delta_{PIVCD}$, referred to a paced interventricular conduction delay (PIVCD) or, more generally an interventricular conduction delay (IVCD or $\Delta_{IVCD}$). FIG. 5 pertains to pacing in a right ventricle and sensing in a left ventricle wherein the time between pacing and sensing is referred to as a right to left PIVCD or PIVCD-RL, which equals $R_{LV}-V_{RV}$, wherein $V_{RV}$ is a pace time of a pacing stimulus in the right ventricle and $R_{LV}$ is a sense time of an evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices, systems, etc., include a capture algorithm (e.g., autocapture). Various exemplary methods related to capture are discussed further below. Also, as already mentioned, an IVCD typically depends on position of an electrode as well as electrode configuration. Hence, where the $V_{RV}$ location and the LV sense location are close together, then IVCD-RL may be shorter than if the $V_{RV}$ location and the LV sense location were spaced further apart.

FIG. 5 shows a set of waveforms 510 that include an atrial event (e.g., A or P), an atrial to ventricular paced delay $AV_{RV}$, a ventricular pace time $V_{RV}$ and a sensed evoked response in the right ventricle $ER_{RV}$. Another set of waveforms 520 pertains primarily to the left ventricle and includes an atrial event (e.g., A or P), an AVN delay and a sensed evoked response in the left ventricle $R_{LV}$ which is a result of the stimulus $V_{RV}$ in the right ventricle. To ensure that the sensed evoked response in the left ventricle $R_{LV}$ is not due to conducted electrical activity from the atria, a sufficiently short ventricular paced delay $AV_{RV}$ is used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

FIG. 6 pertains to pacing in a left ventricle and sensing in a right ventricle wherein the time between pacing and sensing is referred to as a left to right PIVCD or PIVCD-LR, which equals $R_{RV}-V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, PIVCD-LR is normally greater than zero. To ensure that the pacing stimulus in the left ventricle results in an evoked response, a capture routine or algorithm may be implemented. Thus, various exemplary methods, devices, systems, etc., include a capture algorithm (e.g., autocapture). Various exemplary methods related to capture are discussed further below. Also, as already mentioned, an IVCD typically depends on position of an electrode as well as electrode configuration. Hence, where the $V_{LV}$ location and the RV sense location are close together, then IVCD-RL may be shorter than if the $V_{LV}$ location and the RV sense location were spaced further apart.

FIG. 6 shows a set of waveforms 620 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 610 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 70 ms may suffice. In one example, $AV_{LV}$ is set to approximately 50 ms to approximately 80 ms. $AV_{LV}$ may also be set sufficiently short to avoid fusion. While AV is referred to, PV may also apply where appropriate.

In general, bipolar sensing (or other multipolar/combipolar sensing) may increase signal to noise of the sensed activation response in the left ventricle when compared to unipolar sensing that includes use of an in vivo, yet non-local electrode such as a pulse generator can. The latter technique is often more used in detection of evoked response or the applications utilizing far-field signals. Further, bipolar sensing that includes two electrodes positioned in proximity to each other (e.g., less than approximately 4 cm), may increase signal to noise and sensitivity and better localize an activation wavefront.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

Figure 7:
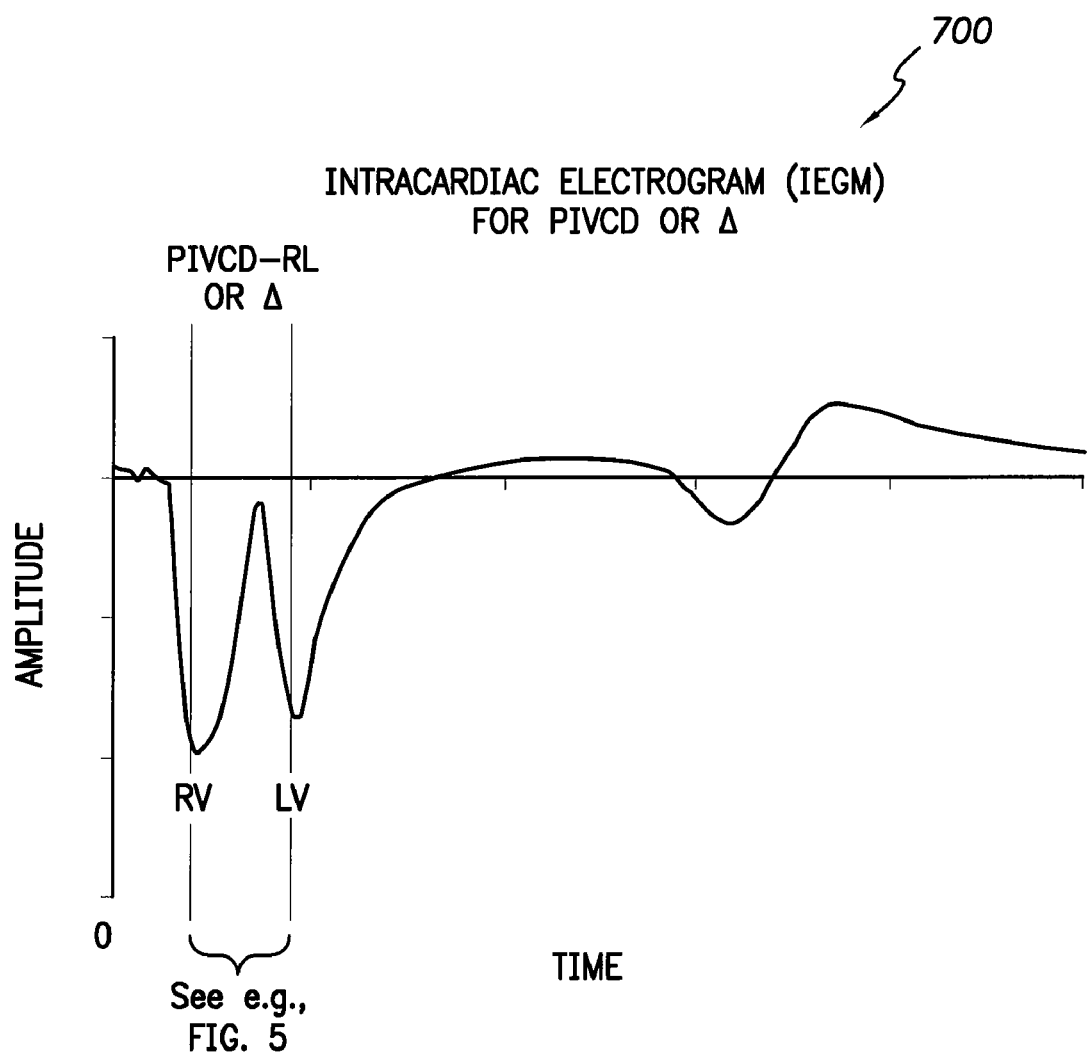
FIG. 7 is an exemplary IEGM plot acquired in a study using a unipolar sensing arrangement for a right ventricular tip electrode and a left ventricular tip electrode having a common electrode.

FIG. 7 shows an exemplary IEGM plot 700 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle, and is identified by the two discernible peaks shown in FIG. 7 and corresponding to right ventricular activation and left ventricular activation, respectively. In this example, the peak-to-peak time delay typically approximates $\Delta$ and may be used to determine whether the lead positions are suitable. However, it may approximate PIVCD-RL in the case of FIGS. 5 and 6. If RV is paced at a short AV delay (such that no intrinsic conduction will have yet arrived at the ventricles), the time delay from pacing RV to the peak of the conduction to the left ventricle approximates PIVCD-RL. In an alternative example, not shown in FIG. 13, a pacing stimulus may be delivered to the right ventricle at a time of approximately 0 ms. This pacing stimulus will result in capture of the right ventricle and the IEGM will show a corresponding right ventricular evoked response. In this example, the left ventricle is not paced or initially captured by the pace to the right ventricle but after a short delay, the left ventricle will depolarize due to conduction of the paced event from the right ventricle. Hence, the delay between the right ventricular peak (RV) and the left ventricular peak (LV) approximates a paced interventricular conduction delay from right ventricle to left ventricle (see, e.g., PIVCD-RL of FIG. 5). Thus, the plot 700 helps to demonstrate a particular exemplary manner in which an implantable device that uses a single sensing amplifier for right and left ventricular sensing channels can determine paced interventricular conduction delay.

Further, some implantable devices having sensing and pacing capabilities can deliver a stimulus to one ventricle and then switch to sensing of both ventricles. For example, in the plot 700, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 8:
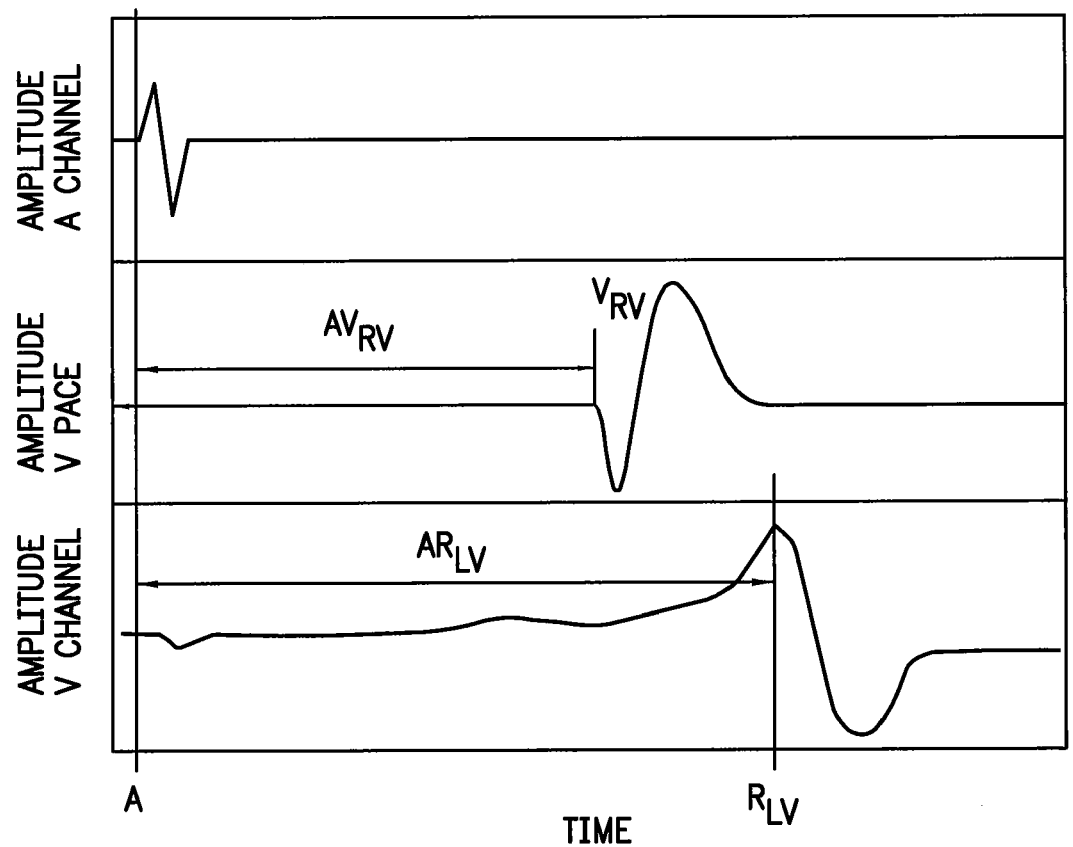
FIG. 8 is an exemplary atrial and ventricular IEGM plot acquired in a study using an implantable device optionally including a switchable channel for RV and LV sensing and/or pacing.

FIG. 8 shows an exemplary IEGM plot 800 wherein the ventricular IEGM was acquired using an implantable device including a switchable channel for RV and LV sensing. Such a device may allow for measurement of $AR_{RV}/PR_{RV}$ and $AR_{LV}/PR_{LV}$ by switching between RV sensing to LV sensing.

Accordingly, Δ may be ascertained. Such a device may also allow for pacing in the right ventricle and/or left ventricle. Further, such a device may ascertain PIVCD-RL and/or PIVCD-LR. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, PIVCD-RL may equal $AR_{LV}-AV_{RV}$ or $PR_{LV}-PV_{RV}$. As already mentioned, an IVCD may stem from an atrial stimulus (paced or intrinsic) conducted to a ventricle (i.e., the "paced" ventricle of a PIVCD) which subsequently conducts to the other ventricle (i.e., the sensed ventricle of a PIVCD).

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices, systems, etc., may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

Figure 9A:
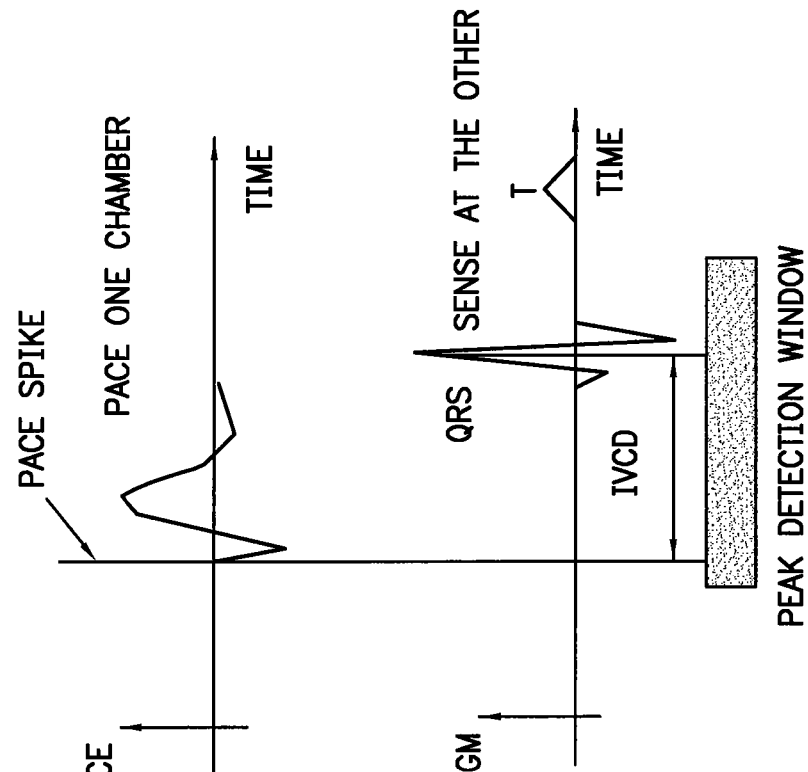
FIGS. 9A and 9B depict ventricular activity as sensed by independent sense channels and illustrate an embodiment in which the atrial activity is not required.
Figure 9B:
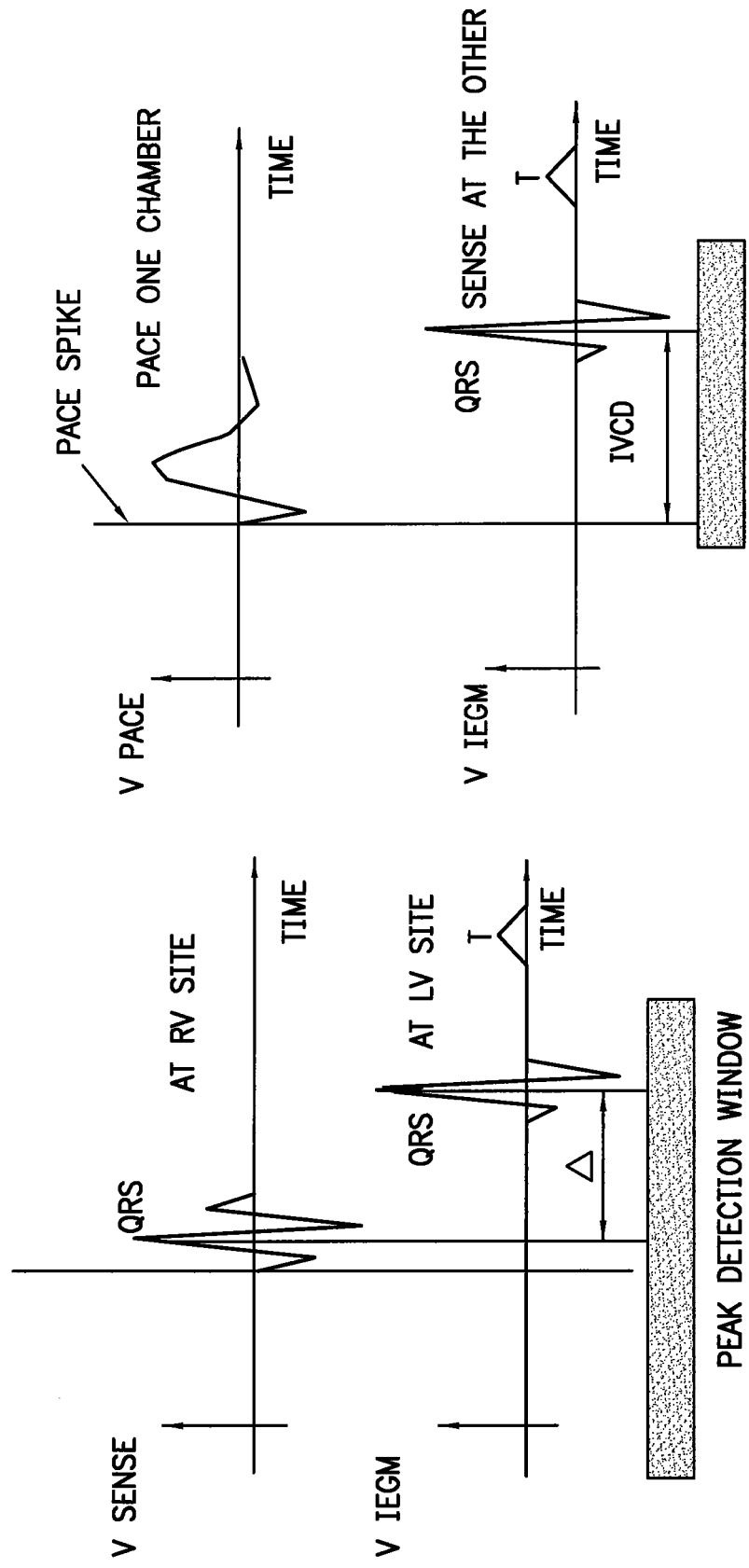

FIGS. 9A and 9B show exemplary IEGM plots 900 of ventricular activity as sensed by a pair of sensing channels, V SENSE and V IEGM. This ventricular activity may be used in one embodiment that does not rely on atrial activity to determine the IVCD or Δ; rather, by simply monitoring the right ventricular and left ventricular activity, the IVCD or Δ value can be determined. As shown in FIG. 9A, the Δ value can be determined by monitoring a first channel (the "V SENSE" channel) for right ventricular activity and a second channel (the "V IEGM" channel) for left ventricular activity. While many different ways of detecting activity can be employed, in this embodiment the peaks are used to detect activity, and the peak-to-peak interval is used to determine the Δ value. In addition, while the RV is shown as being the first ventricle to intrinsically activate, it will be understood that in some patients the LV may activate prior to the RV.

As shown in FIG. 9B, a ventricular pace spike in one chamber (e.g., the right ventricle) initiates the IVCD interval, and detection of the peak of the QRS on the V IEGM channel signifies the end of the IVCD interval. Alternatively, capture verification may be performed in the first chamber (e.g., to detect the peak of the evoked response), and the IVCD interval can be initiated at that point rather than upon delivery of the pacing pulse.

Figure 10:
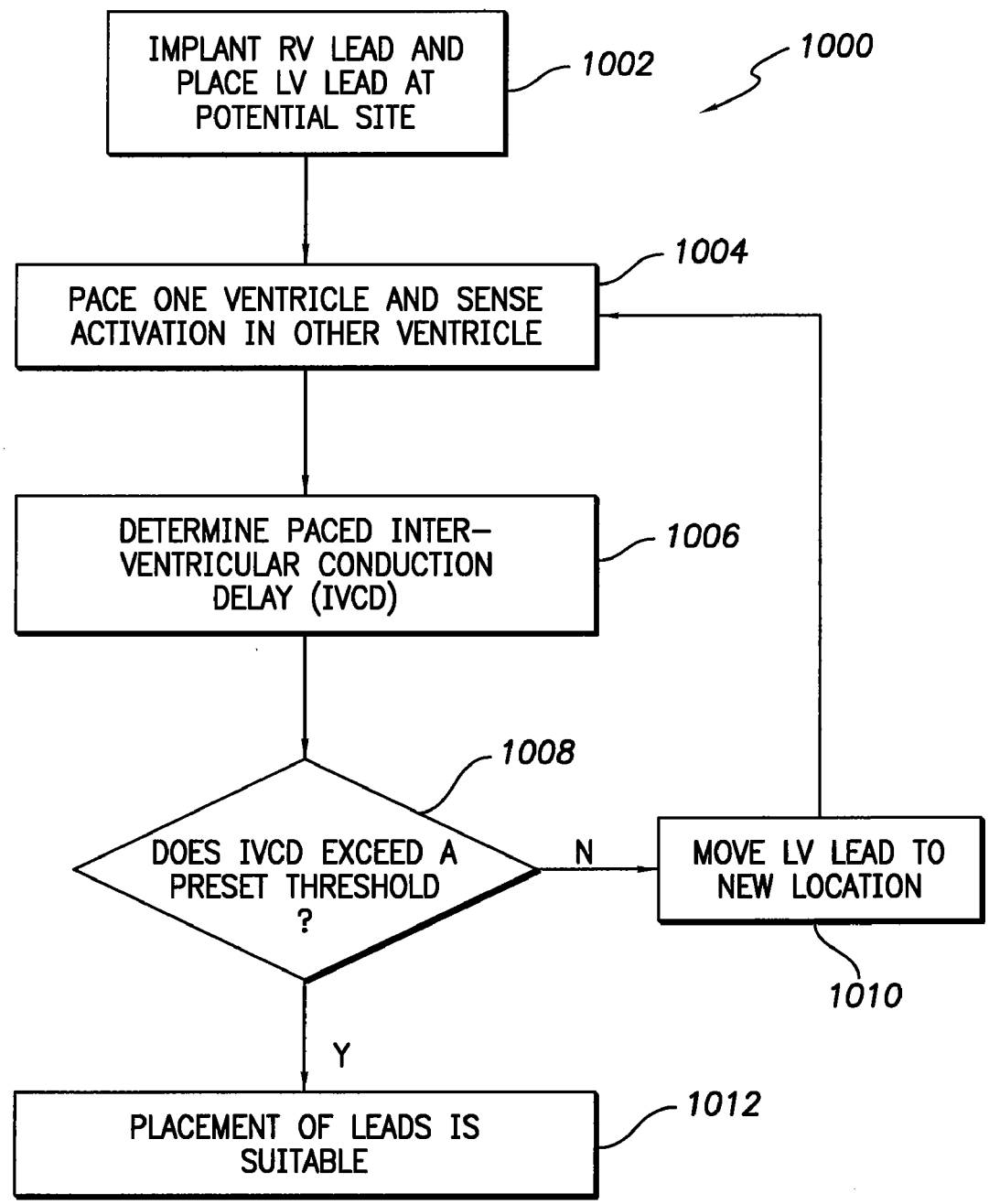
FIG. 10 is a flow chart of another exemplary method for determining whether electrode placement is suitable for CRT therapy.

Referring now to FIG. 10, an illustrative method is shown for determining the suitability of a particular lead placement. As already mentioned, IVCDs depend on electrode position and/or electrode configuration. Consequently, an IVCD may be used as one measure in determining an appropriate lead or electrode position or electrode configuration. At step 1002, the clinician implants an RV lead for stimulating the right ventricle, and locates an LV lead at a first potential site for sensing activity of the left ventricle (e.g., through the coronary sinus, epicardially, pericardially, etc.). At step 1004, a stimulation pulse is delivered to the left ventricle to cause the ventricle to depolarize, and RV activity is detected when the resulting depolarization waveform conducts from the left to the right ventricle. This embodiment is used for patients who suffer from LBBB or other left-sided conduction problems. For patients suffering from RBBB or other right-sided conduction problems, the right ventricle is paced and the corresponding activity is sensed in the left ventricle.

At step 1006, the interval between delivery of the stimulation pulse in the one ventricle and the sensed activity in the other ventricle is determined to be the IVCD. At decision block 1008, a determination is made whether the IVCD exceeds a threshold value. In one embodiment, the threshold value is on the order of 50 to 100 milliseconds, preferably about 80 milliseconds. Thus, if the IVCD does not exceed the threshold, operation proceeds to step 1010 and the system recommends to the clinician that one or both of the electrodes be moved to a new location. Once a new location or locations are found, operation returns to step 1004 and the process is repeated.

If, on the other hand, the IVCD value does exceed the threshold value, operation proceeds to step 1012 and the clinician is advised that the placement is suitable for CRT therapy. The clinician may then continue to implant the medical system and program the implantable medical device, including programming interval values for delivering CRT therapy.

As described above, for patients suffering from RBBB or other right-side conduction problems, the LV lead may be implanted in a desired location, and the RV lead may be advanced to a first potential site for testing, with the above-described method being carried out with LV pacing and RV sensing to determine IVCD values; if the IVCD value does not exceed a threshold value, the RV lead may be moved until a suitable IVCD value is identified. Alternatively, if the RV lead includes a plurality of electrodes, one or more different electrodes may be selected or, in general, an electrode configuration may be changed, the IVCD measured, compared to a threshold and then a decision made as to whether any further changes are warranted. A similar procedure may be used for an LV lead. Further, such techniques may be used if an epicardial electrode of other type of electrode is used for cardiac pacing.

FIG. 11 shows a flow chart of a method for determining proper electrode placement according to another illustrative embodiment. According to the method, the electrodes are placed for communication with the RV and LV, respectively, at step 1102. In one embodiment, the clinician implants the RV lead in the right ventricle and the LV lead is advanced through the coronary sinus and into one of the coronary veins that overlie the left ventricle and into a first potential site to be tested. The clinician then connects the RV and LV leads to a suitable test device, for example, either the implantable medical device, an external pacing system analyzer, the programmer through a suitable adapter, or any other suitable device for processing the sensed IEGM data.

At step 1104, the intrinsic conduction delay Δ is determined based on the interval between activity detected in the RV and activity detected in the LV. For example, the test device may passively monitor the cardiac activity and detect intrinsic activity of the RV and LV, where the delay Δ is computed as the interval between RV and LV activation. In another embodiment, the test device determines an $AR_{RV}$ time and an $AR_{LV}$ time (or a $PR_{RV}$ time and a $PR_{LV}$ time) and computes Δ as the difference between the two values ($AR_{RV}-AR_{LV}$ or $PR_{RV}-PR_{LV}$).

At step 1104, the system optionally determines the order in which intrinsic activity was detected in the right and left ventricles (i.e., which ventricle experiences intrinsic activity first and which one experiences intrinsic activity last) if it has not already been determined a priori. For a patient known to have LBBB or RBBB, for example, this determination will not be necessary as the clinician already knows which ventricle is too slow in activating. This information can be used in step 1110 to determine which ventricle to pace and which ventricle to sense for determining an IVCD value, as described in greater detail below.

At decision block 1106, a determination is made whether Δ exceeds a threshold value, for example 30 milliseconds. If so, operation proceeds to step 1108 and the placement is deemed suitable for CRT therapy. An optional message may be displayed on a user interface to indicate as such to the clinician.

In one embodiment, the delay value preferably exceeds a threshold value, which may range between about 20 and about 60 milliseconds, preferably about 30 milliseconds.

In another embodiment, the delay value is preferably within a range of values, for example between about 20 milliseconds and about 200 milliseconds, more preferably between about 30 and about 160 milliseconds. If the delay value does not exceed the lower limit of the range, operation proceeds to step 1110 as described below. In addition, if the delay value exceeds the upper limit of the range, then the system recommends that one or both of the electrodes be moved to new locations.

On the other hand, if Δ does not exceed the threshold value, operation instead proceeds to step 1110. At step 1110, the system determines the IVCD value by the following procedures:

1) delivering a stimulation pulse (preferably at a very short AV delay) to the ventricle that experienced intrinsic activity last;

2) sensing corresponding activity in the other ventricle (i.e., the ventricle that intrinsically activated first); and 3) determining an interval between either A) the delivery of the pulse in the first ventricle and detection of activity in the other ventricle, or B) verification of capture in the first ventricle and detection of activity in the other ventricle.

In one embodiment, where intrinsic activity is detected last in the LV, the pacing pulse is delivered to the LV in a subsequent cycle and at a short AV delay, and the conducted activity is sensed in the RV (IVCD-LR). Alternatively, where intrinsic activity is detected last in the RV, the RV is paced at a short AV delay and the conducted activity is sensed in the LV (IVCD-RL).

The IVCD is then compared with a threshold at query block 1112. The threshold may differ depending upon which interval calculation method was used. For example, the threshold can be on the order of about 60 to about 100 milliseconds, and preferably about 80 milliseconds, when the interval is between delivery of the pulse and detection of activity in the other ventricle. On the other hand, the threshold can be on the order of about 30 to about 50 milliseconds, and preferably about 40 milliseconds, when the interval is between verification of capture in the first ventricle and detection of activity in the other ventricle.

If the IVCD exceeds the threshold, then operation proceeds to step 1108 and the placement is considered suitable for CRT therapy. If not, operation proceeds to step 1114 and the clinician is alerted that one or more of the electrodes should be moved. In one embodiment, the clinician will move the LV lead, either to a new location within the same cardiac vein or withdraw it from the cardiac vein and then advance it through a different cardiac vein. Once the clinician has moved the lead to the next proposed location, operation returns to step 1104 and the process is repeated. If no suitable location is found after multiple sites are tested, the clinician may either withdraw the LV lead and implant an epicardial lead, or choose one of the tested sites and program the implantable medical device with the knowledge that the site may not be optimal for CRT therapy.

It will be understood by those skilled in the art that the sensing described herein can be done in a unipolar configuration, i.e., between an electrode implanted in the heart and the device housing, or in a bipolar configuration, i.e., between a pair of electrodes implanted in the heart. Bipolar sensing can be done with a truly bipolar lead (having a tip electrode and closely spaced ring electrode), or an integrated bipolar lead (having a tip electrode and a defibrillation coil used to sense electrical activity).

In an alternate embodiment, one or both of the RV and LV leads can be epicardial leads connected to the outside of the heart over the RV and LV, respectively, or one or both of the RV and LV leads can be replaced by satellite electrodes that telemeter information to a remote device.

As mentioned above, in some implant procedures the LV lead will be implanted prior to the RV lead, and it will be desirable to test the location of the LV lead, and possibly reposition it as necessary, prior to implanting the RV lead. In that case, a surface ECG signal may be used in place of the RV lead. In particular, a vector may be chosen that replicates the IEGM signal detected by an RV lead at the RV apex, for example lead V2, lead V1, lead V3, and/or lead II.

Figure 12:
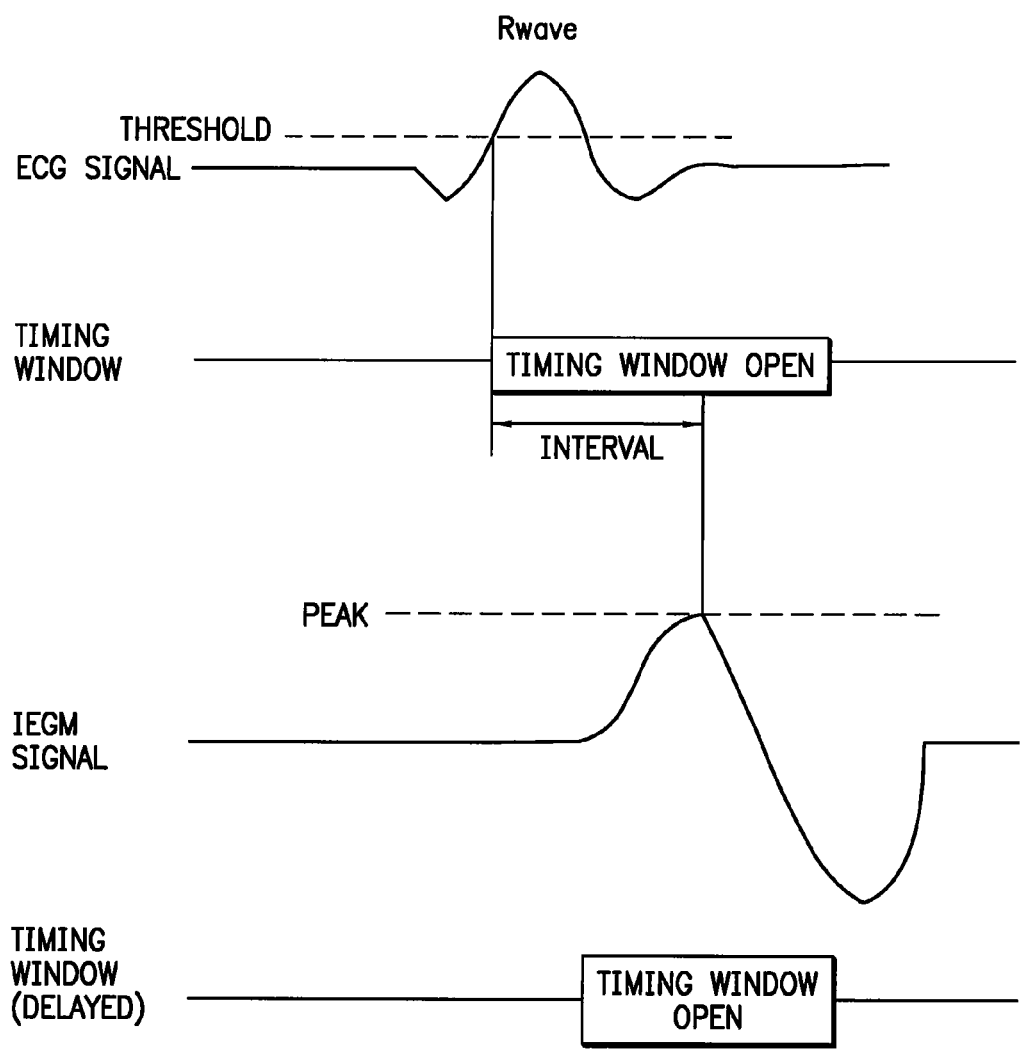
FIG. 12 is an exemplary plot of ECG and IEGM data to be used in accordance with another exemplary method.
Figure 13:
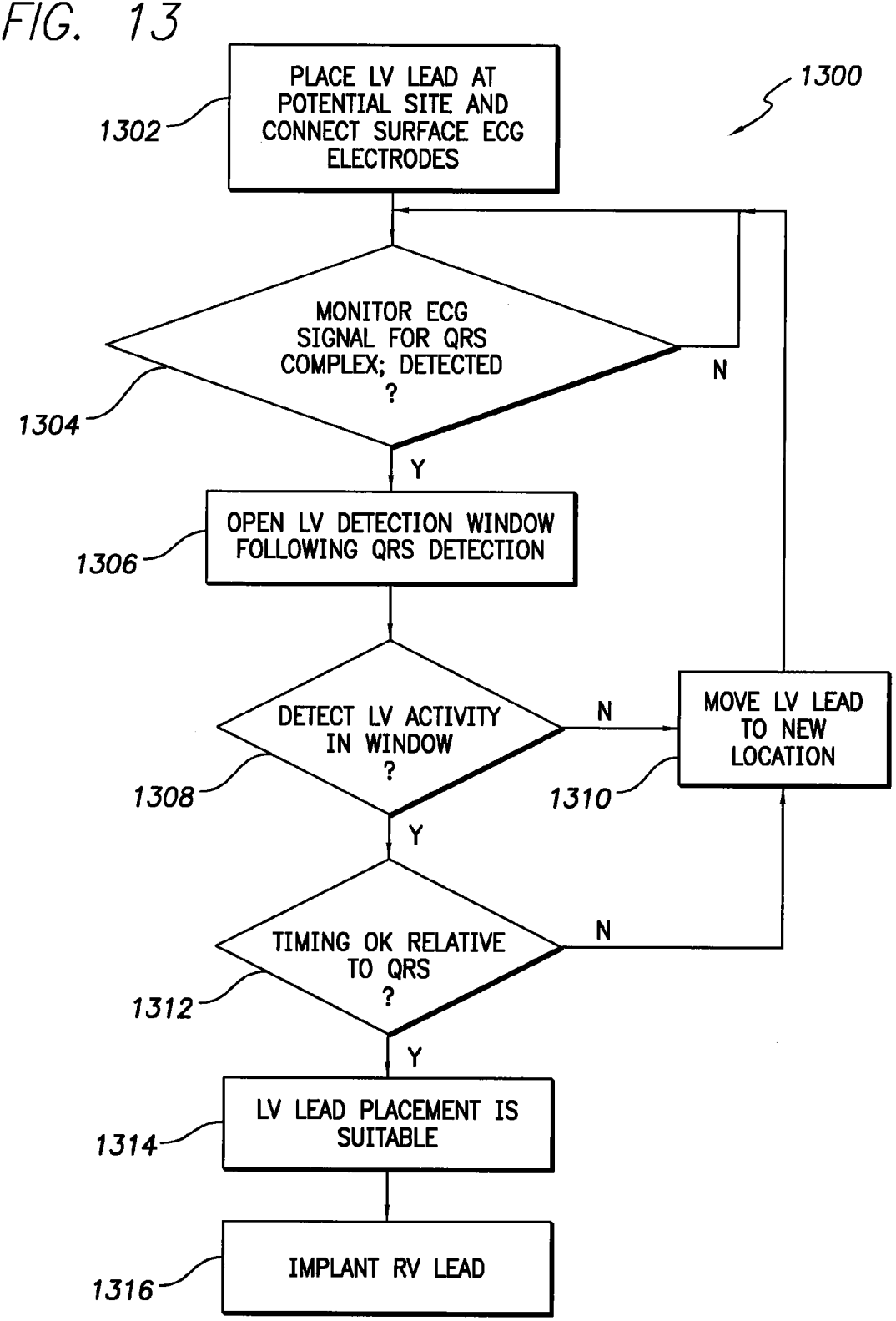
FIG. 13 is a flow chart of a method that uses the data from FIG. 12.

Referring to FIGS. 12 and 13, another embodiment is disclosed that addresses the situation where the LV lead is temporarily positioned and it is desired to test such placement prior to implanting the RV lead. As shown in FIG. 12, a surface ECG is preferably monitored to detect a QRS complex. Upon detection of the QRS complex (e.g., when the ECG signal exceeds the amplitude threshold), a timing window is opened to monitor for activity sensed by the LV lead. Preferably, the LV activity (in one embodiment detected by a peak of the LV activity signal) will occur toward the end of the window, corresponding to a sufficiently large Δ value; if it occurs too early in the window, the LV electrode placement will be deemed unacceptable for CRT therapy. An interval 1202 (corresponding to the Δ value) may be computed between detection of ventricular activity from the ECG signal and corresponding left ventricular activity detected by the IEGM signal. The interval may be compared with a threshold, as described in detail above.

Alternatively, the window may be delayed following the detection of the QRS complex (see the Timing Window (alternate)), for example approximately 30 milliseconds, and if no activity is detected within the window, then the activity either occurs too early or too late and another site is recommended. If activity is detected within the window, then the electrode placement is deemed suitable.

As shown in FIG. 13, operation begins at step 1302 with the clinician locating the LV lead at a first potential site, and attaching the surface ECG electrodes to the patient. At query block 1304, the system monitors the ECG signal for a QRS complex. Upon detection of the QRS complex, operation proceeds to step 1306, and the system opens a window to monitor the LV lead for detection of left ventricular activity. As described above, the window may be opened immediately following the QRS detection, or may be delayed a predetermined period of time.

At query block 1308, if no LV activity is sensed within the window, then operation proceeds to step 1310 and a different placement is recommended for the LV electrode. On the other hand, if LV activity is detected within the window, operation proceeds to optional step 1312, where the timing of the LV activity is compared to the QRS detection. As mentioned above, when the opening of the window is delayed following QRS detection, step 1312 is unnecessary. If the window is opened immediately following QRS detection, then step 1312 is preferably included. If the timing of the LV activity relative to the QRS detection (e.g., if the interval between QRS detection and LV activity is sufficiently long) then operation proceeds to step 1314 and the electrode placement is deemed suitable. If not, operation instead proceeds to step 1310 and a different electrode placement is recommended.

Once the LV site is selected, operation proceeds to step 1314, and the RV electrode is implanted in the RV. In one embodiment, the RV electrode is placed using the ECG and LV IEGM information as a reference. Alternatively, the RV electrode location can be selected to further increase the separation between detected RV activity and LV activity.

It will be understood by those skilled in the art that the analysis of the electrode placement can be performed by any device that is able to receive electrical signals from the electrodes and process the signals to determine cardiac timing information. For example, the method can be carried out by the implanted pacemaker or defibrillator, which analyzes the information and then may telemeter such information to a programmer or other external device. In addition, the electrodes may be temporarily connected to a pacing system analyzer (PSA), directly to the programmer, or to any other device capable of processing the sensed cardiac activity (see, e.g., the system and description of FIG. 24).

It will be understood by those skilled in the art that while the various embodiments are described primarily for patients who suffer from LBBB and who therefore have late-acting left ventricles, the same embodiments can be applied to patients who suffer from RBBB and who therefore have late-acting right ventricles. In those patients, the various embodiments are applied in reverse, i.e., 1) the LV lead is implanted, 2) the RV lead is located at a potential site, 3) the $\Delta$ value and/or IVCD value are determined, and 4) to RV lead is moved to a new site if the $\Delta$ value and/or IVCD value do not exceed the respective threshold(s).

In yet another embodiment, the system may determine a $\Delta$value, an IVCD value for right ventricular pacing and left ventricular sensing (IVCD-RL), and an IVCD value for left ventricular pacing and right ventricular sensing (IVCD-LR). Only if each value exceeds a corresponding threshold will the location(s) be deemed suitable; if not, one or both of the RV and LV electrodes will be moved to new locations, and the values recalculated.

The above-described method for improving response to CRT therapy can also be used for other features utilized by implantable cardiac devices. Consider a technique that uses such timing parameters ($\Delta$, IVCD-RL, IVCD-LR) and one or more corresponding thresholds to decide whether beat-to-beat capture detection may be suitably performed or to decide whether a specialized capture detection method may be implemented. With respect to capture detection or verification, consider biventricular capture verification, and especially beat-to-beat, biventricular capture verification. As will be apparent to those skilled in the art, if the $\Delta$value is too small, an evoked response sensed in a first chamber may be corrupted by applied stimulation in the second chamber causing fusion, or by far-field sensing in the first chamber of the applied stimulus. Similarly, if IVCD-RL or IVCD-LR is too small (e.g., sensing electrodes/leads too close), then a sensed evoked response for one ventricle may appear fused with and a sensed evoked response for the other ventricle. Therefore, the methods described herein may be used to determine whether an existing electrode placement is suitable for performing biventricular capture verification, or to determine whether one or more electrodes should be moved in order to improve the likelihood of being able to successfully perform capture verification. Alternatively, or in addition to, where feasible, a change may occur in an electrode configuration for sensing.

Thus, in one embodiment for use in connection with biventricular capture verification, the right-sided electrode and left-sided electrode are placed, and the IVCD value is measured. If the IVCD exceeds a preset threshold (e.g., one or more of the thresholds described above), then the placement is considered suitable for performing biventricular capture verification. If not, either 1) a clinician is alerted that one or more of the electrodes should be moved, 2) the clinician is advised that biventricular capture verification should not be performed given the electrode spacing, or 3) the implanted device may automatically disable the biventricular capture verification feature. Thus, the clinician may move the left-side electrode, with the process being repeated until a suitable spacing is found.

Various exemplary methods, devices, systems, etc., pertain to assessing whether a patient is likely to respond to CRT or whether a patient responds to CRT. An exemplary model relies on EGM information, which may be acquired during implant or after implantation of a device. The model optionally includes a parameter that relies on both EGM information and ECG information. In general, each parameter corresponds to a measure based on acquired information. For example, an exemplary model uses the delay $\Delta$, the IVCD-RL, the IVCD-LR, and/or the $\Delta_{IVCD}$ as measures. Based on the value of each measure, the model may assign a value to a corresponding parameter, which, in turn, is used to calculate a score (e.g., a score value). The score may be compared to may be compared to past scores for the patient, scores from other patients, one or more theoretical scores, etc. Individual measures may also be compared to past measures for the patient, measures from other patients, one or more theoretical measures, etc. Such a comparison or comparisons may help guide a clinician as to treatment options.

Consider the following exemplary model:
Measures: $\Delta$, IVCD-RL, $\Delta_{IVCD}$, % $R_{ECG}/QRS_{ECG}$
Parameters: P-$\Delta$, P-IVCD-RL, P-$\Delta_{IVCD}$, P-%
Assignment of Values:
If $\Delta$>80 ms then P-$\Delta$=1, else 0
If IVCD-RL>130 ms then P-IVCD-RL=1, else 0
If 50 ms<$\Delta_{IVCD}$<100 ms then P-$\Delta_{IVCD}$=1, else 0
If % $R_{ECG}/QRS_{ECG}$>50% then P-%=1, else 0
Calculation of Score:

$$Score = P\text{-}\Delta + P\text{-}IVCD\text{-}RL + P\text{-}\Delta_{IVCD} + P\text{-}\%$$

Thus, if a patient had a score of 4, then it is likely that the patient will respond to CRT. As described below, a model may not explicitly use parameters but rather calculate a score directly from a value of a measure where the value is based on acquired information. In either instance, a model provides a score based on acquired information where the acquired information includes EGM information and optionally ECG information or other information.

The discussion that follows summarizes various parameters and surface ECG techniques. Various exemplary methods, devices, systems, etc., are then described where IEGM and/or surface ECG information may be used for predicting whether a patient is likely to respond to CRT, response to CRT, etc.

In the foregoing example of a model, various measures were used to determine a score. However, an exemplary model may use any of a variety of measures where at least one measure includes EGM information. Such EGM information may be acquired at implant or after implantation of a device. A review of various measures follows, some of which have already been described above.

Table 1, below, classifies sinus activity, paced activity and other activity for the atria and the ventricles, assuming that ventricular activity does not cause atrial depolarization. Classifications include primary events (1°), secondary events (2°) and tertiary events (3°). For example, sinus activity (P) is a primary event (1°) of the atria and, more particularly, the right atrium. Sinus activity is, in general, never a primary event (1°) of either ventricle. Instead, sinus activity (P) normally causes a secondary event (2°) of a ventricle or, where a block may exist, a tertiary event (3°) of a ventricle. For example, for a patient with left bundle branch block, sinus activity (P) causes a secondary event (2°) for the right ventricle and where depolarization of the right ventricle (R) causes depolarization of the left ventricle ($R_C$), depolarization of the left ventricle is a tertiary event (3°). In this example, and various others, the subscript "C" refers to conducted, i.e., an event in the right ventricle conducted to the left ventricle and caused depolarization of the left ventricle (e.g., $R_C$ or $ER_C$, depending on whether the origin was atrial or via a delivered ventricular stimulus). Subscripts may be added to V, ER, R, $R_c$, $R_V$, or $ER_c$ to denote association with the right ventricle (RV) or the left ventricle (LV).

TABLE 1

Classification of Activity

| Origin | Sinus | Paced | Other (e.g., PVC) |
|---|---|---|---|
| Right Atrium | 1° (P) | 1° (A) | 1° |
| Right Ventricle | 2° (R)<br>3° ($R_C$) | 1° (V, ER)<br>2° (R, $R_V$, $ER_C$)<br>3° ($R_C$) | 1°, 2°, 3° |
| Left Ventricle | 2° (R)<br>3° ($R_C$) | 1° (V, ER)<br>2° (R, $R_V$, $ER_C$)<br>3° ($R_C$) | 1°, 2°, 3° |

The various events can be used to determine intervals. For example, a PR interval, a $PR_c$ interval, an $RR_c$ interval, an AV interval, a $VR_V$ interval, etc. Where ventricle designators are used, these examples may become for the right ventricle $PR_{RV}$, $PR_{C-RV}$, $R_{RV}R_{C-LV}$, $AV_{RV}$, $V_{RV}R_{V-LV}$, etc., and for the right ventricle $PR_{LV}$, $PR_{C-LV}$, $R_{LV}R_{C-RV}$, $AV_{LV}$, $V_{LV}R_{V-RV}$, etc.

An interventricular conduction delay (IVCD) may be a sensed interventricular conduction delay (SIVCD) where an intrinsic event in one ventricle conducts to the other ventricle. For example, where atrial activity (1° event) occurs in the presence of a bundle branch block, the ventricle without block may be expected to depolarize (2° event) followed by the ventricle with block (3° event). Thus, a sensed interventricular conduction delay may be the interval R to $R_c$ (e.g., SIVCD=$R_c$-R) where $R_c$ corresponds to an R-wave for a conducted depolarization of a ventricle.

Again, for pacing in a right ventricle and sensing in a left ventricle, the time between pacing and sensing is referred to as a right to left PIVCD or PIVCD-RL, which equals $R_{V-LV}$-$V_{RV}$, wherein $V_{RV}$ is a pace time of a pacing stimulus in the right ventricle and $R_{V-LV}$ is a sense time of a "right ventricle, evoked response wavefront" in the left ventricle due to the paced stimulus in the right ventricle. In general, this wavefront is co-extensive with depolarization of the left ventricle and hence referred to as an $R_V$ wave or $ER_c$ (i.e., a conducted evoked response).

Various delays and other measures or parameters are discussed herein such as the following delays that are related to pacing in the right ventricle and/or the left ventricle:

| | |
|---|---|
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| $\Delta$ | Estimated interventricular delay, e.g., via IEGM, etc. |
| $\Delta_{programmed}$ | Programmed interventricular delay (e.g., a programmed VV delay) |
| $\Delta_{optimal}$ | Optimal interventricular delay, e.g., via hemodynamic sensing/sensor or other cardiac sensing |
| IVCD-RL | Delay between paced/sensed RV and sensed LV |
| IVCD-LR | Delay between paced/sensed LV and sensed RV |
| $\Delta_{IVCD}$ | Interventricular conduction delay (paced, sensed, hybrid) |

As indicated, in some instances $\Delta_{IVCD}$ may be a hybrid of a PIVCD time and a SIVCD time (both being IVCD times). Other measures include those already mentioned (e.g., $R_V$ or $ER_C$) as well as those conventionally used in conjunction with cardiac activity (e.g., AR, PR, etc.). In addition, measures such as $AR_V$ or $PR_V$ and yet others may be used.

A description of ECG information follows that indicates various ECG measures that may be used in an exemplary model. As described herein, surface ECG information can be helpful in assessing response to CRT, cardiac condition, selecting a lead position, an electrode position, an electrode configuration, etc.

While various examples refer to ECG information acquired using cutaneous electrodes (e.g., a surface ECG), an exemplary method may optionally use an electrode configuration where at least two of the electrodes are widely spaced, for example, an electrode configuration that uses an intracardiac electrode (e.g., SVC coil) and a case electrode of an implantable device. A cardiac electrogram acquired using such an electrode configuration may be optionally used as a surrogate for an ECG acquired using cutaneous electrodes. In particular, such an electrode configuration is likely to provide a QRS complex having a width approaching that of an ECG acquired using cutaneous electrodes. Thus, where the measure % $R_{EGM}$/$QRS_{ECG}$ appears, a surrogate may be % $R_{EGM-1}$/$QR$-$S_{EGM-2}$ where EGM-1 uses a first electrode configuration (e.g., "near-field") and EGM uses a second electrode configuration (e.g., "far-field").

Figure 14:
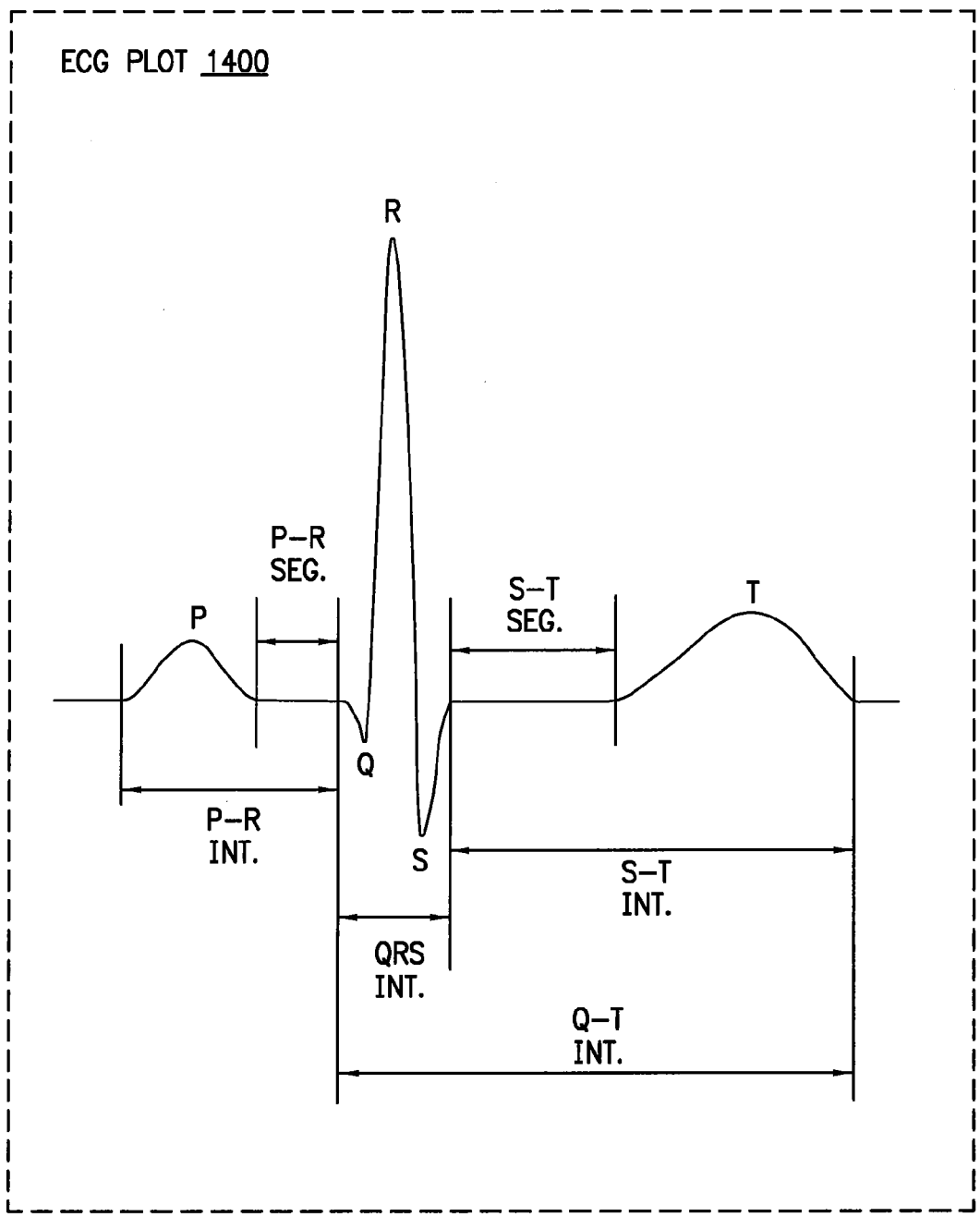
FIG. 14 is a plot of an ECG that identifies various features, including peaks and intervals.

FIG. 14 shows a plot 1400 of a stylized surface ECG for one cardiac cycle. The plot 1400 includes various peaks, segments and intervals, some of which have been mentioned above. While one plot is shown in FIG. 14, depending on specific features of the ECG acquisition system used, multiple plots may be acquired. For example, a multiple lead ECG acquisition system can acquire multiple plots for a single cardiac cycle. In general, each plot is associated with a different lead configuration and hence shapes and timings of the various peaks, segments and intervals may vary from plot to plot.

Most ECG acquisition systems rely on multiple leads. For example, one fairly standard multiple lead ECG acquisition system relies on 7 leads while another relies on 12 leads. The standard 7 lead system includes leads labeled I, II, III, aVR, aVL and aVF while the standard 12 lead system also includes leads labeled V1 through V6. The labels correspond to surface positions with respect to the body.

Given this brief background on multiple lead ECG acquisition systems, the various components of the ECG plot 1400 are now described. The peak labeled "P" corresponds to a P wave caused by depolarization of the atrial myocardium. A normal P wave usually has a width of less than about 110 ms. Depending on lead configuration, a P wave is usually positive and rounded in leads I, II, and aVF in about 94% of normal individuals and usually negative in aVR. The P wave axis is about 60°.

An interval that is measured from the beginning of a P wave to the beginning of the QRS complex, is referred to as the PR interval, which represents atrial depolarization plus an AV nodal delay. The PR interval is typically in a range from about 120 ms to about 200 ms. Where AV conduction is impaired, the PR interval is lengthened (e.g., first-degree AV block). The PR interval includes the PR segment, which begins at the end of the P wave and ends with the onset of the QRS complex. Elevation of the PR segment may indicate disease such as atrial infarction or pericarditis. Depression of the PR segment may occur if a large atrial repolarization wave exists.

While labeled as individual peaks in the plot 1400, the QRS complex represents depolarization of the ventricular myocardium. While depolarization of the AV node, His bundle, bundle branches, and Purkinje fibers also occurs, the electrical signals emerging from these cardiac structures are typically too small in amplitude to be detected by electrodes on the body surface.

According to some conventions, positive waves of the QRS complex are labeled R waves. Further, if more than one positive peak exists, then the second positive peak is labeled R'. In some conventions, an upper case capital letter "R" is used to describe a sizable R wave and a lower case letter "r" is used to describe a small R wave. Negative waves of the QRS are typically labeled with "Q", referred to as Q waves, which precede the R wave or labeled with "S", referred to as S waves, which follow the R wave. Again, relative size may be denoted by use of upper or lower case letters. Although termed the "QRS" complex, many complexes do not contain all three waves distinctly.

A "normal" QRS complex from a surface ECG will typically have a width ranging from about 70 ms to about 110 ms. Some conventions for 12-lead ECG measurements consider the widest QRS measurement as the most correct. Many consider leads I and V1 as providing the most accurate QRS complex width. Various exemplary methods may use a QRS width from any of the conventional lead arrangements and/or from specialized lead arrangements.

In a multi-lead measurement system, a progression typically occurs for the R wave. In the precordial leads, the QRS complex starts off primarily negative (rS) in V1 and gradually becomes primarily positive (qRs) with the tallest R wave in V5 or V6. The transition from mostly negative to mostly positive typically occurs between V3 and V4. Normally the R wave in V6 is always less in magnitude than the R wave in V5. Precordial R waves are usually sensitive to lead placement, a factor that should be considered for interpretation of R wave progression.

Various conditions may be determined on the basis of the R wave or R wave progression. For example, an early R wave in leads V1 and V2 having a magnitude as large as those in the next several leads (e.g., V3, V4, V5) can reflect posterior infarction, lateral MI, right ventricular hypertrophy (RVH), or septal hypertrophy. Also consider a large magnitude R wave in V1, which may indicate RVH, posterior MI, or Wolff-Parkinson-White (W-P-W).

Small magnitude R waves in the right precordial leads may be due to left ventricular hypertrophy (LVH), left anterior fascicular block (LAFB), COPD, or MI. LVH causes loss of R wave magnitude from V1-V3 without MI. Loss of R magnitude between V1-V2 or V2-V3 in the absence of LVH suggests anterior MI.

A poor R wave Progression, e.g., R waves that do not begin to dominate the QRS complex until V5 or V6, may represent infarction or injury of the anterior LV.

With respect to the Q Wave, not all leads may record a Q wave. Normal Q waves typically represent septal depolarization. Q waves should be distinguished from pathologic Q waves that can indicate myocardial infarction.

A "normal" Q wave is usually present in leads I, aVL, V5, and V6 (left lateral leads) only and has a width of about 4 ms. A small Q wave may be evidenced in aVF and V5 leads. Lack of a Q wave may indicate septal fibrosis; whereas, a large Q wave (magnitude), may indicate myocardial damage, as large, diagnostic Q waves represent altered electrical activity in the myocardium due to transmural myocardial damage. Note however that a diagnostic Q wave in V1, aVL, or III may be present without indicating myocardial damage.

An ST segment commences at the "J point" (end of the QRS complex) and ends at the onset of the T wave. The ST segment represents the duration for which ventricular cells are in the plateau phase (phase 2) of the action potential (where there is no current flow and thus little, if any, transmembrane gradient). QRS complex width and ST segment also represent the duration of the ventricular absolute refractory period, where the ventricles will generally not respond to stimulation. The ST segment should be isoelectric with a smooth contour. In instances where it is not isoelectric, the ST segment may be characterized as ST depression or ST elevation.

The QT Interval is a measure of the refractory period during which the myocardium would not respond to a second impulse and it is typically measured from the beginning of the QRS complex to the end of the T wave. Some consider leads V2 or V3 as providing the most accurate QT interval. A basic rule indicates that the QT interval should be roughly less than half the preceding RR interval. QT interval normally varies with heart rate. QT interval may also be affected by width of the QRS complex such as a bundle branch block, which increases the QT interval. Thus, ST interval may be considered to compensate for a wide QRS complex.

A measure referred to as QT dispersion is determined on the basis of QT intervals from various (or all) ECG leads where the shortest QT interval ($QT_{Min}$) is subtracted from the longest QT interval ($QT_{Max}$). A substantial difference between these two QT intervals may indicate that heterogeneous refractoriness exists and that the patient may be at higher risk of cardiac death from development of ventricular tachycardia/fibrillation, especially from any proarrhythmic effects of antiarrhythmic drugs.

JT intervals may be measured to reflect repolarization. The JT interval is sometimes used to measure the refractory period in patients treated with a Na+ channel blocker antiarrhythmic drugs (e.g., Quinidine, Pronestyl, and other class I agents), which slow depolarization and prolong the QRS complex.

The T wave represents repolarization of the ventricles and the earliest the ventricles can respond to another stimulus usually coincides with the apex of the T wave. The T wave should have the same polarity as the QRS complex, i.e., if the QRS complex is primarily negative, the T wave should be negative.

ST deviation and T wave abnormalities are seen with conditions other than myocardial ischemia such as a wide QRS complex or secondary to effects of medications. It is possible to have both primary and secondary changes (e.g., bundle branch block plus ischemia). In this case, the ST segment may appear to normalize because both ST depression and elevation are occurring simultaneously.

Where various ECG signals are available (e.g., from a multi-lead ECG system), R peaks, PR intervals, PR segments, QRS intervals, QR intervals, RS intervals, ST intervals, QT intervals, etc., may be used to assign a probability of responding to CRT or make another type of assessment with respect to CRT. Dispersions, subtractions, additions, ratios, maxima, minima, etc., of the aforementioned measures may be used. With respect to subtractions, where the value of RS interval minus QR interval is greater than a certain value (e.g., a threshold), then this may indicate a greater likelihood of responding to CRT. Thus, an exemplary method optionally relies, at least in part, on a difference between QR interval and RS interval. Of course, use of QRS interval may substitute for QR interval or RS interval (e.g., QR interval=QRS interval−RS interval).

With respect to maxima, an exemplary method optionally determines a maximum RS interval from multi-lead ECG information and then assigns a probability of responding to CRT and/or selects one or more CRT settings based at least in part on the maximum RS interval. For example, the maximum RS interval may be compared to predetermined ranges or values or may be compared to historical values to assign a probability or to make a selection of a CRT setting.

In some instances, a subject may have a narrow QRS yet still benefit from CRT. In such instances, the aforementioned % $R_{EGM}/QRS_{ECG}$ measure may help assess response to CRT (see also FIGS. 17 and 18). As described herein, determinations and analyses of measures such as RS interval alone or with reference to one or more other measures, may help identify such subjects and optionally help in selecting one or more CRT settings.

While various measures have been mentioned with respect to one or more surface ECGs (e.g., depending on number of leads, etc.), other measures may be used, alternatively, or in addition to the aforementioned measures. For example, the time of a peak in a wave (e.g., R wave peak time), the time for a maximum in dV/dt, time, the time of commencement of a wave (e.g., R wave commencement time), the time of an end of a wave (e.g., R wave end time), differences between various times (e.g., difference between peak of an R wave and end of an R wave).

Various leads were mentioned with respect to the ECG plot 1400 of FIG. 14. FIG. 15 shows an arrangement 1500 referring to a body 1501 with placement positions for 7 leads and a volumetric coordinate system 1540 associated with the positions and the heart. Each lead perceives the heart electrically from a particular point of view. Leads II, III and aVF perceive the inferior surface while leads I and aVL perceive the left lateral wall. Again, most graphical representations of an ECG use a lead I representation.

The body 1501 further indicates approximate positions for the heart 1502 and the lungs 1504. The lead positions are indicated by circles, where one circle has a dashed line as it is positioned on the backside of the body 1501.

The coordinate system 1540 indicates approximate positions for the four chambers of the heart and a central conduction path with right and left ventricular branches. The acronym aVL refers to "augmented voltage left", the acronym aVR refers to "augmented voltage right" and the acronym aVF refers to "augmented voltage foot".

The foregoing discussion with respect to FIG. 14 may be referenced to the various ECG plots 1610 of FIG. 16 (see also coordinate system of FIG. 15). FIG. 16 also includes a diagram of exemplary locations 1640 that indicate approximate placement positions for the percordial leads V1-V6, noting that they may be in approximately the same plane or not. The ECG plots 1610 include peak R wave labels $R_I$, $R_{II}$, $R_{III}$, $R_{aVR}$, $R_{aVL}$, $R_{aVF}$ for respective lead/electrode positions 1500 of FIG. 15 and peak R wave labels $R_1$, $R_2$, $R_3$, $R_4$, $R_5$ and $R_6$ for the respective lead/electrode positions 1640 of FIG. 16.

ECG information is electrical information. This information inherently reflects mechanical information of the heart. Exemplary measures such as R, ΔR (e.g., spread of R-wave over a series of lead/electrode positions), QRS width uncover cardiac mechanics. In particular, exemplary measures such as ΔR may uncover ventricular mechanics (e.g., synchrony, dyssynchrony).

While the foregoing discussion of ECG information pertains mainly to ventricular mechanics, such information may aid in determining one or more stimulation sites for stimulation of the right ventricle and/or the left ventricle.

Various studies have presented models that use ECG information to assess cardiac condition. Consider a review by Wellens and Gorgets ("The Electrocardiogram 102 Years After Einthoven," *Circulation* 2004 109: 562-564) that discusses various efforts to relate ECG measures to cardiac condition. For example, a ST segment deviation score can help estimate the size of an area at risk of myocardial infarction. The ST segment deviation score is determined by counting the number of millimeters (on a chart) that the ST segment deviates (elevated or depressed) from the isoelectric line in a 12-lead ECG where the higher the ST-segment deviation number, the larger the area at risk. An exemplary model may use such ECG information to determine a score for response to CRT.

As electrical activity of the heart must conduct through the body to reach an ECG lead/electrode, some signal dispersion occurs. In contrast, an implantable lead/electrode may acquire an EGM signal with little dispersion, especially where electrodes are located near a focus of electrical activity. Hence, surface ECG information may be considered far-field while EGM information may be considered near-field; noting that electrode configurations may exist for acquiring far-field EGM information. For example, near-field EGM information may use a bipolar electrode configuration where the electrodes are spaced within about a centimeter of each other (e.g., $RV_{tip}$ and $RV_{ring}$) whereas far-field EGM information may use a unipolar electrode configuration where the electrodes are spaced more than about 5 cm from each other (e.g., can and $RV_{tip}$, can and SVC coil, etc.).

Figure 17:
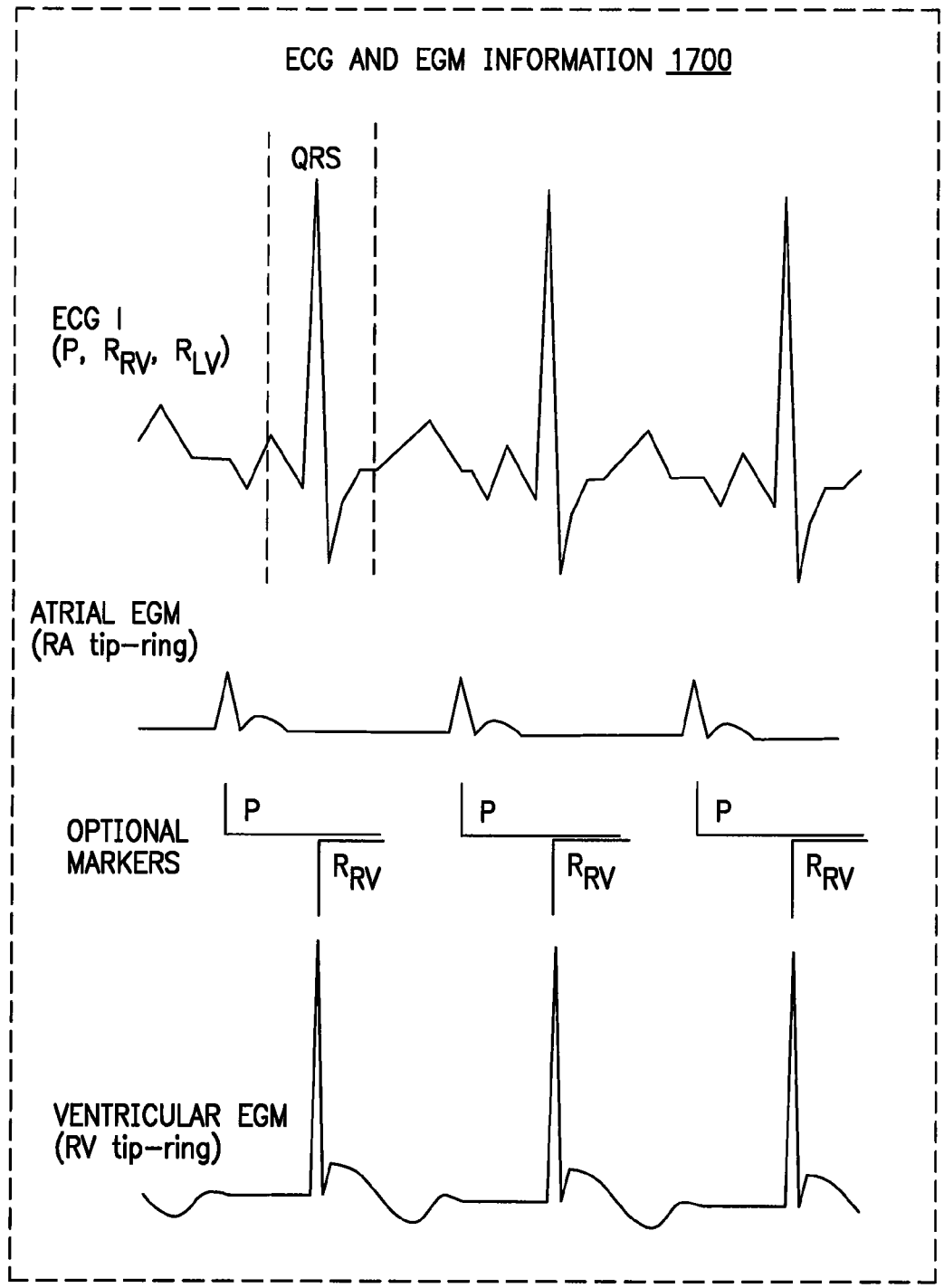
FIG. 17 is a series of plots that include a surface ECG, an atrial channel EGM and a ventricular channel EGM of right ventricular data.

FIG. 17 shows plots 1700 of ECG information and EGM information. More specifically, the plots 1700 include an ECG I (including a mix of signals for P, $R_{RV}$, $R_{LV}$ waves), an atrial EGM ($RA_{tip}$ to $RA_{ring}$) and a ventricular EGM ($RV_{tip}$ to $RV_{ring}$). Also included are optional markers to indicate timing of P-waves (P) and right ventricular R-waves ($R_{RV}$). An exemplary implantable device may include instructions to assign timings and present labels. An exemplary device programmer or other computing device may include such features as well (see, e.g., system 2400 of FIG. 24).

Of particular note in the plots 1700 is the relationship between the QRS width and the timing of $R_{RV}$. Where available, a left ventricular EGM may be acquired that exhibits $R_{LV}$. Further, an RV lead/electrode may be capable of sensing $R_{LV}$ and an LV lead/electrode may be capable of sensing $R_{RV}$.

Figure 18:
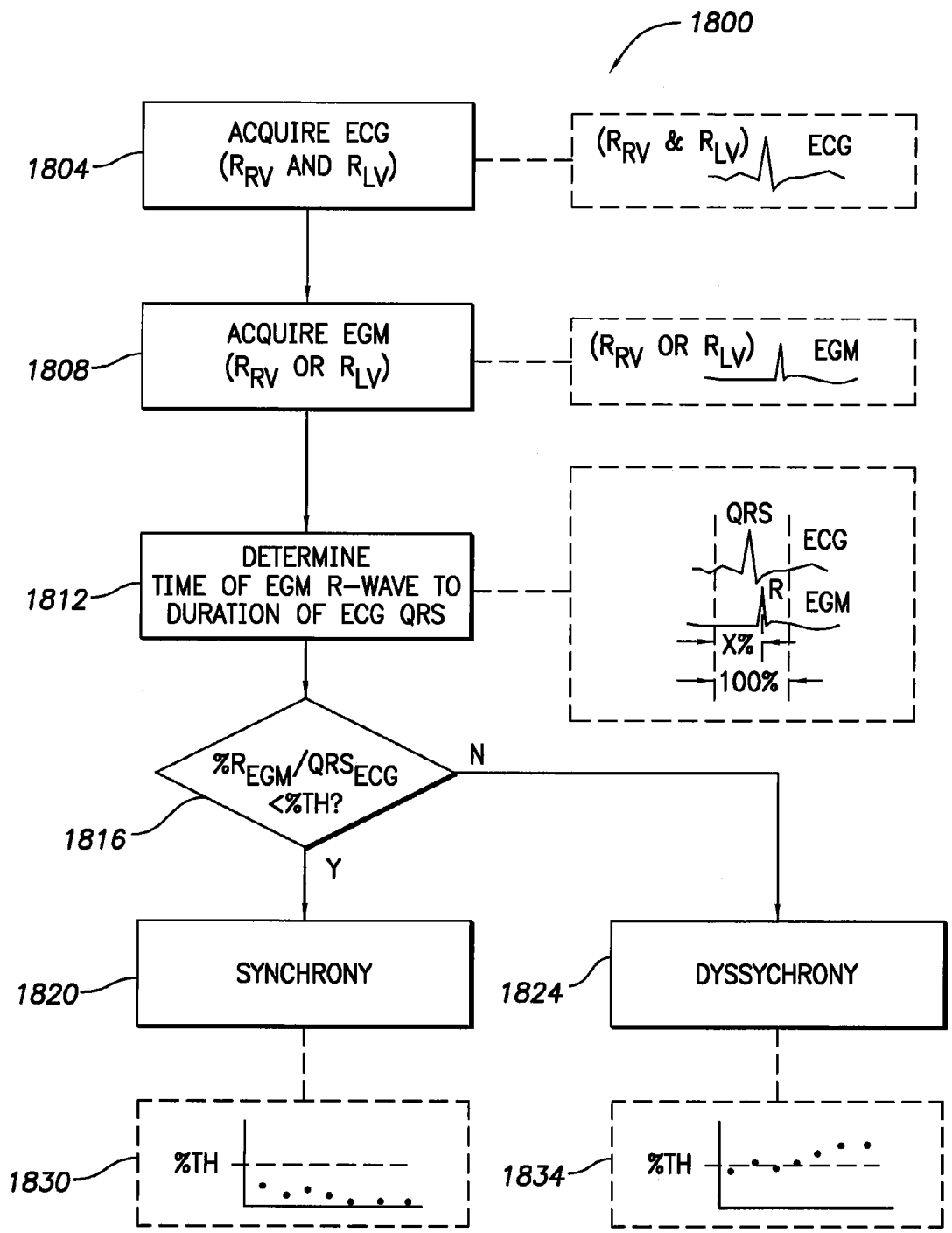
FIG. 18 is a flow chart of an exemplary method that uses QRS width of a surface ECG and timing of an R-wave of an EGM to determine whether synchrony or asynchrony exists.

FIG. 18 shows an exemplary method 1800 for determining the aforementioned % $R_{EGM}/QRS_{ECG}$ measure. The method 1800 commences in an acquisition block 1804 that acquires ECG information, for example, representative of $R_{RV}$ and $R_{LV}$. Another acquisition block 1808 acquires EGM information that exhibits $R_{RV}$ and/or $R_{LV}$. A determination block 1812 uses the ECG information to determine duration or width of a QRS complex and uses the EGM information to determine timing of $R_{RV}$ or $R_{LV}$. Then the determination block 1812 determines the measure % $R_{EGM}/QRS_{ECG}$ based on the R-wave timing and the QRS width. A plot associated with the block 1812 presents QRS width as 100% and the R-wave timing as occurring at X % of the QRS width.

A decision block 1816 follows that decides whether the % $R_{EGM}/QRS_{ECG}$ measure (e.g., X %) is less than a threshold (e.g., % Th). The threshold may be a first, predetermined percentage or fraction of the QRS complex width. For example, if a parameter % Th is set to 50%, then the decision block 1816 decides if X % is less than 50%. If the decision block 1816 decides that the measure (e.g. X %) is less than the threshold (e.g., % th) then synchrony exists per declaration block 1820, otherwise dyssynchrony exists per declaration block 1824. In either instance, the measure may be plotted over time as indicated by plots 1830 and 1834. Such an analysis may indicate whether a patient's ventricular contractions are becoming more or less synchronous.

An exemplary method may include detecting a QRS complex using cutaneous electrodes, during the QRS complex, detecting an R-wave of a ventricle using an intracardiac electrode, determining if the R-wave occurred during a first percentage of the QRS complex width (e.g., some predetermined percentage, % Th) and, based at least in part on the determining, deciding whether a patient is likely to respond to cardiac resynchronization therapy. In this example, the predetermined percentage may be approximately 50% or another value (e.g., based on patient data for responders and non-responders to CRT). The intracardiac electrode may be an epicardial electrode, an electrode positioned in a cardiac chamber, an electrode positioned in a venous structure, etc.

Figure 19:
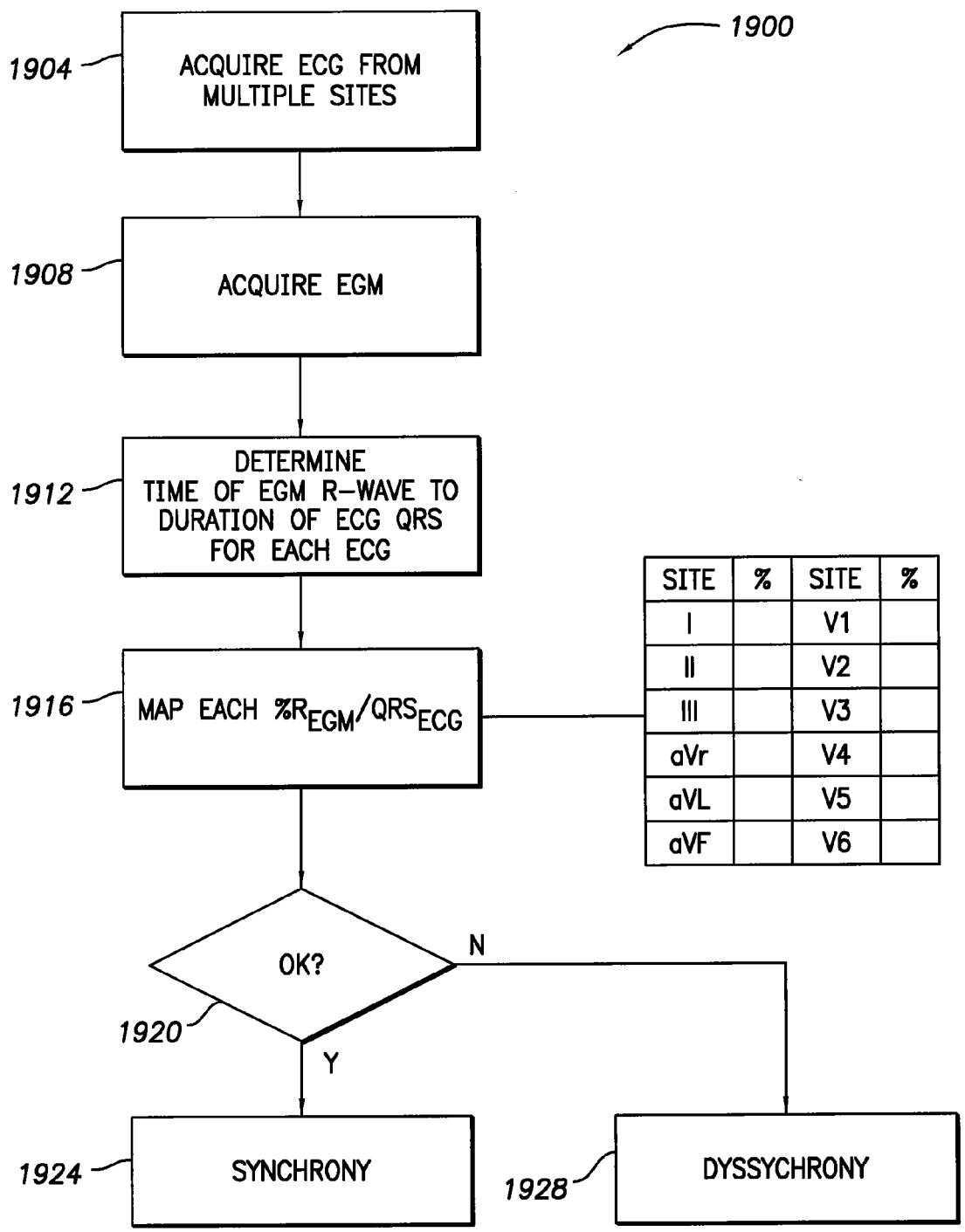
FIG. 19 is a flow chart of an exemplary method that uses QRS widths from multiple surface ECGs and timing of an R-wave of an EGM to determine whether synchrony or asynchrony exists.

FIG. 19 shows an exemplary method 1900 that acquires ECG information from multiple sites per an acquisition block 1904. another acquisition block 1908 EGM information. A determination block 1912 uses the ECG information to determine, for each site, duration or width of a QRS complex and uses the EGM information to determine timing of $R_{RV}$ or $R_{LV}$. Then the determination block 1912 determines multiple % $R_{EGM}/QRS_{ECG}$ measures based on the R-wave timing and the multiple QRS widths. For example, each QRS width may be set to 100% and the R-wave timing used to determine X % of the QRS width for each QRS width (e.g., $X_I$%, $X_{II}$%, $X_{aVR}$%, etc.). A mapping block 1916 maps each measure to a corresponding ECG site. Each of these measures may have a corresponding threshold percentage (e.g., % $Th_I$, % $Th_{II}$, etc.) or a common threshold percentage may be used.

A decision block 1920 uses the mapped measures (e.g., per the map table associated with block 1916) to decide if a patient's ventricular contractions occur synchronously (block 1924) or asynchronously, i.e., "dyssynchronously" (block 1928).

An exemplary method may include detecting a QRS complex using cutaneous electrodes, during the QRS complex, detecting an R-wave of a ventricle using at least one intracardiac electrode, for each of a plurality of cutaneous electrode configurations, determining a percentage for the timing of the R-wave with respect to the total width of the QRS complex for a respective cutaneous electrode configuration and, based at least in part on the determining, deciding whether contraction of the ventricles occurred synchronously. According to such a method the plurality of cutaneous electrode configurations may include one or more of the following ECG configurations: I, II, III, aVR, aVL, aVF, V1, V2, V3, V4, V5 and V6.

FIG. 20 shows a right ventricular data table 2010 and a left ventricular data table 2020 where an ECG site and an EGM site are listed for a given measure (e.g., % $R_{EGM}/QRS_{ECG}$, etc.). The data table 2010 indicates that RV EGM sensing occurred using an $RV_{Tip-Ring}$ electrode configuration while the data table 2020 indicates that LV EGM sensing occurred using various LV electrode configurations: $LV_{Coil-Ring-1}$, $LV_{Tip-Ring-1}$ and $LV_{Tip-Ring-2}$. Other configurations may be used, as appropriate. Further, a given ECG site may have more than one corresponding EGM site. Thus, a data table may be of a different size, number of columns, number of rows, etc. The particular configurations chosen may be based on patient responder/non-responder information, device configuration, etc.

Figure 21:
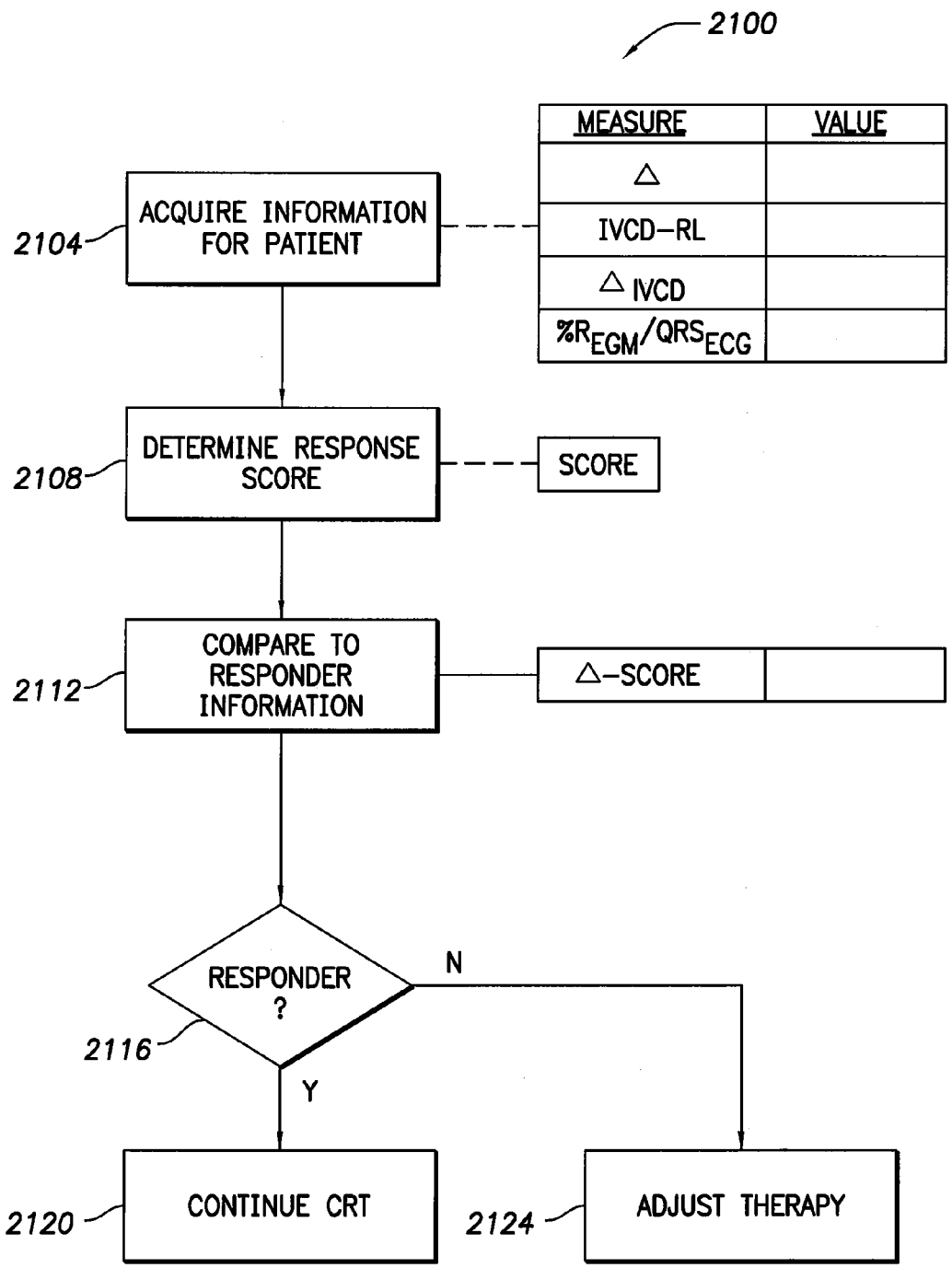
FIG. 21 is a flow chart of an exemplary method that uses a model for scoring a patient to decide if the patient is a responder.

FIG. 21 shows an exemplary method 2100 for determining a response score and taking action based on the score. The method 2100 commences in an acquisition block 2104 that acquires information for a patient. An associated data table provides examples of such information. In particular, the table includes the measures of the model presented above: $\Delta$, IVCD-RL, $\Delta_{IVCD}$, % $R_{ECG}/QRS_{ECG}$. A determination block 2108 determines a score based on the acquired information. For example, the block 2108 may use the model presented above to determine a score.

Once the score has been determined, a comparison block 2112 compares the score to responder information. For example, the comparison block 2112 may compare the score to an average score for patients that respond to CRT. The comparison block 2112 may calculate a score differential (e.g., $\Delta$-score) that indicates a deviation from an average score or threshold score. Such a differential may be used to assign a probability that the patient will respond to CRT.

A decision block 2116 decides, based on the comparison, whether the patient is likely to respond to CRT. If the decision block 2116 decides that the patient is likely to respond or is already responding to CRT, then the method 2100 continue with CRT per the continuation block 2120. However, if the decision block 2116 decides that the patient is not likely to respond, i.e., a non-responder, then the method continues in an adjustment block 2124 that may adjust a patient's therapy based on the decision. In the instance that the patient has already been fitted with an implantable device for administration of CRT, then the adjustment block 2124 may call for adjustment to one or more parameters of the CRT where such adjustment may attempt to improve a patient's response to CRT.

An exemplary method may include providing a model for scoring likelihood of responding to cardiac resynchronization therapy where the model relies on a plurality of parameters, determining one or more parameter values based on cardiac activity information acquired using an implantable device and calculating a score using the model. Such a method may include comparing the score to a threshold. Such a method may include, based at least in part on the comparing, deciding whether a patient is likely to respond to cardiac resynchronization therapy.

With respect to measures or parameters, the model may include at least one of the following: $\Delta$, IVCD-RL, IVCD-LR, $\Delta_{IVCD}$ and/or % $R_{EGM}/QRS_{ECG}$. Hence, cardiac activity information may include an interventricular conduction delay, a paced interventricular conduction delay, etc. ECG information may also be used. The score may be used in deciding whether to adjust a therapy, deciding whether to continue delivery of a cardiac resynchronization therapy, etc.

Figure 22:
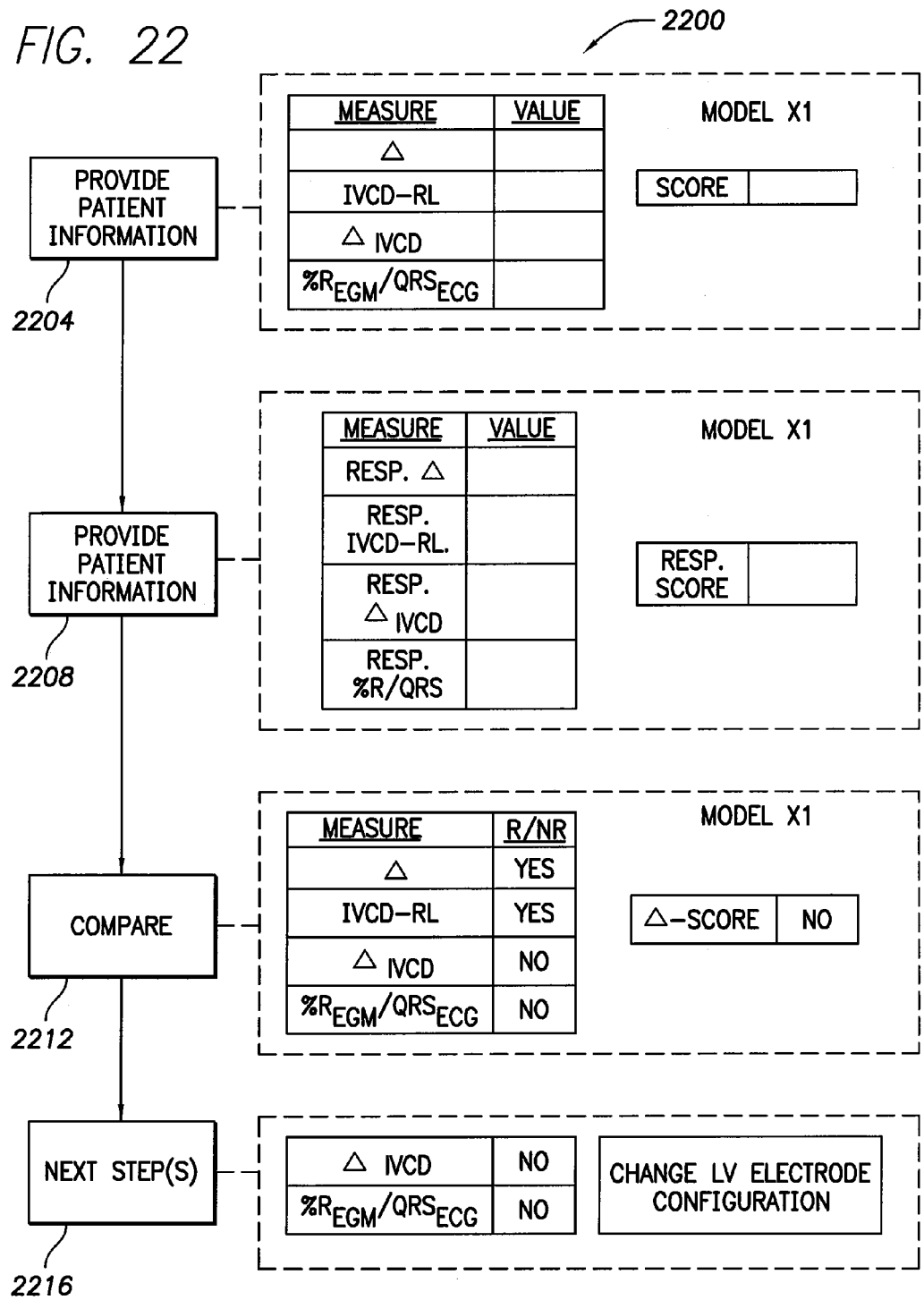
FIG. 22 is a flow chart of an exemplary method that uses a model to score a patient, to decide that the patient is not a responder and to take one or more appropriate next steps based on the model.

FIG. 22 shows an exemplary method 2200 with an example of a next step based on a score. The method 2200 commences in a provision block 2204 that provides patient information such as values for various measures of an exemplary model for determining a responder score. Another provision block 2208 provides responder information such as values for various measures where the values are based on information from patients that respond to a particular therapy (e.g., CRT). The responder information may be based on a statistical analysis of various patient populations which may include non-responders.

A comparison block 2212 compares the patient information to the responder information. While the foregoing model used a "0" and "1" approach, the model of FIG. 22 uses a "Yes" and "No" approach. Of course, various approaches may be used and gradations may be used (e.g., "0.25", "maybe", etc.). The comparison block 2212 indicates that two of the measures indicate that the patient is likely to respond to therapy however two of the measures indicate that the patient is unlikely to respond to the therapy. In this example, a next step(s) block 2216 recommends a course of action: "Change LV Electrode Configuration". Such an action may help produce a more measures, at least for the measures that indicated the patient was unlikely to respond to the therapy.

An exemplary method may include providing patient information where the patient information includes a score and one or more parameters where the score and the one or more parameters indicate a likelihood of responding to cardiac resynchronization therapy, providing responder information where the responder information includes a score threshold and one or more parameter thresholds, comparing the patient information to the responder information and identifying one or more parameters that indicate a diminished likelihood of responding to cardiac resynchronization therapy. Such a method may include, based at least in part on the identifying, adjusting an electrode configuration for sensing cardiac activity. Such a method may include acquiring additional patient information using an adjusted electrode configuration and repeating the comparing using the additional patient information.

Figure 23:
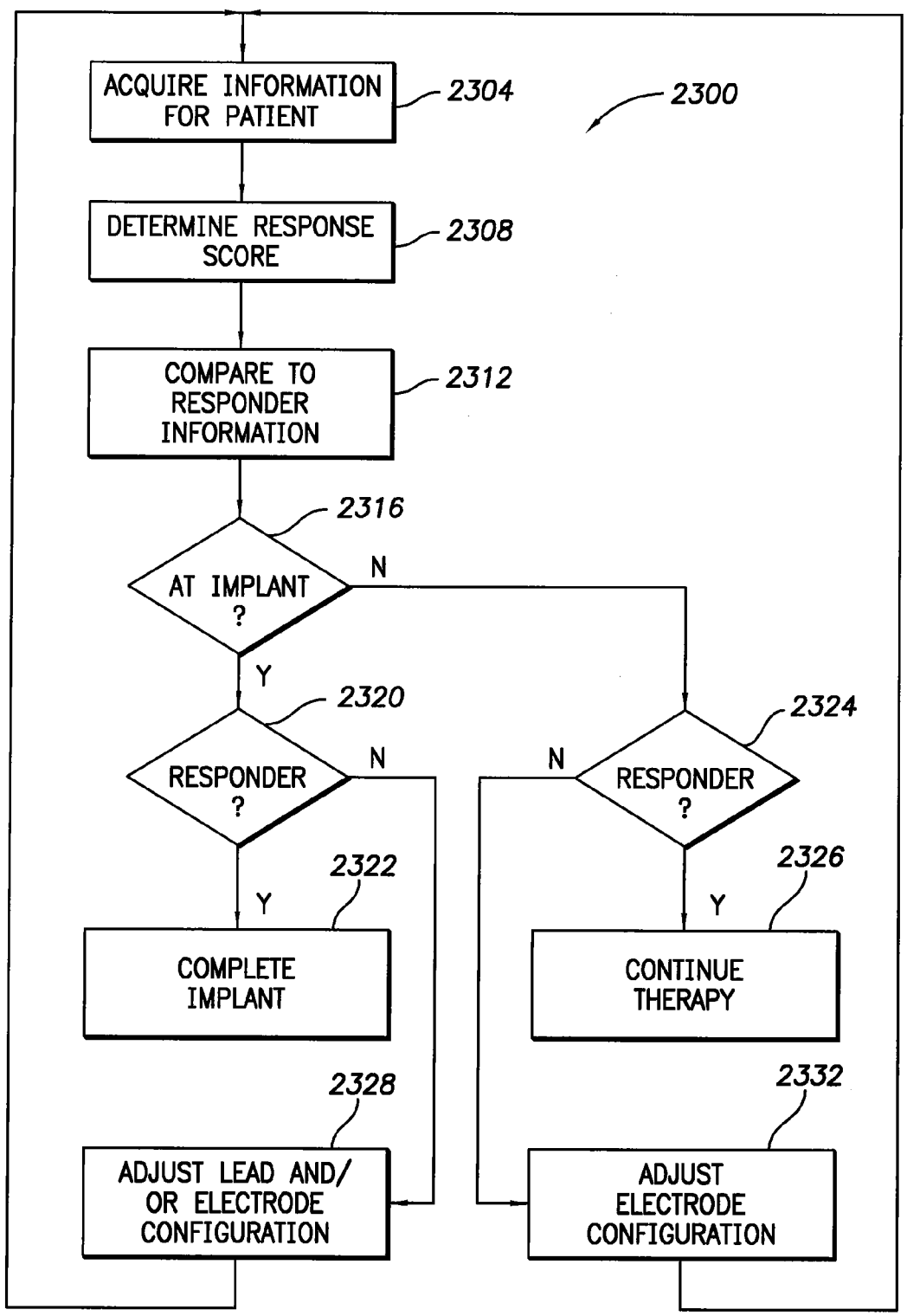
FIG. 23 is a flow chart of an exemplary method that uses a response score during an implant to complete an implant or adjust a lead and/or electrode configuration or uses a response score after implantation to continue therapy or to adjust an electrode configuration.

FIG. 23 shows an exemplary method 2300 that may be used during implant or after implantation of an exemplary implantable device for delivery of cardiac therapy. The method 2300 commences in an acquisition block 2304 that acquires patient information. A determination block 2308 determines a score based on the acquired patient information, for example, using a model. A comparison block 2312 compares the score to responder information. A decision block 2316 follows that decides whether the method is occurs at time of implant or after implant of an exemplary implantable cardiac therapy device.

If the decision block 2316 decides that the method is executing at time of implant, then time of implant options may be selected for example per blocks 2322, 2328; whereas, other options may exist if the method is executing after implantation (e.g., after a patient is removed or recovered from implant surgery) for example per blocks 2326, 2332. In either instance, the method 2300 continues at a respective decision block 2320 or 2324 to decide if the patient information corresponds to a patient that is likely to respond to a therapy (e.g., CRT). If the decision block 2320 decides that the information corresponds to a responder, then the method 2300 continues implant per block 2322. Otherwise, an adjustment block 2328 calls for adjustment of a lead, an electrode, an electrode configuration, etc., which may occur at time of implant.

For the post-implant branch of the method 2300, if the decision block 2324 decides that the information corresponds to a responder, then the therapy continues in a continuation block 2326. If a particular therapy is not enabled or programmed, the continuation block 2326 may enable or program such a therapy for delivery by the implanted device. If the decision block 2324 decides that the information corresponds to a patient unlikely to respond to therapy, then an adjustment block 2332 calls for an adjustment to an electrode configuration. Such an adjustment may act to change a measure and hence a score of the patient.

An exemplary method includes acquiring patient information, determining a score based on the acquired patient information where the score indicates a likelihood of responding to cardiac resynchronization therapy and, for a patient undergoing implantation of an implantable device, if the score indicates a likelihood of response to cardiac resynchronization therapy, completing implantation of the implantable device or, if the score does not indicate a likelihood of response to cardiac resynchronization therapy, adjusting an electrode position or an electrode configuration associated with the implantable device. Such adjusting may adjust position of an electrode-bearing lead. In a post-implant alternative, if the score indicates a likelihood of response to cardiac resynchronization therapy, delivering a cardiac resynchronization therapy or, if the score does not indicate a likelihood of response to cardiac resynchronization therapy, the method may include adjusting an electrode configuration associated with the implantable device.

Figure 24:
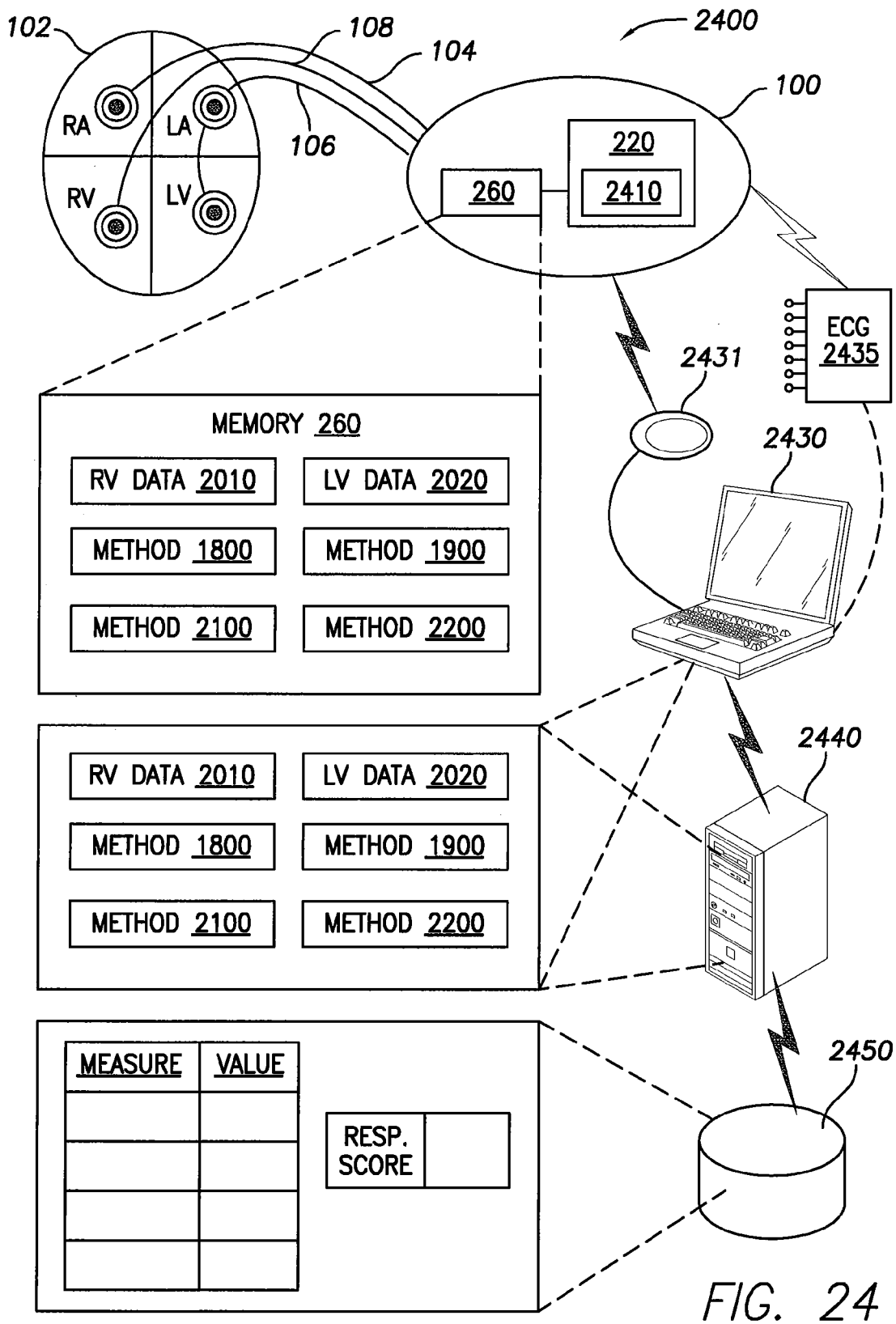
FIG. 24 is a diagram of an exemplary system for use in implementing various exemplary techniques.

FIG. 24 shows an exemplary system 2400 that includes the exemplary implantable device 100 of FIGS. 1 and 2, with processor 220 including one or more modules 2410, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

Memory 260 is shown as including RV data 2010, LV data 2020 where such data may include one or more measures, pacing parameters, historical interval values, etc. Memory 260 also include appropriate modules (e.g., processor-executable instructions) for performing various actions of the methods 1800, 1900, 2100, 2200, etc., noting that part of a method may be performed using a device other than the implantable device 100. For example, for acquisition of ECG information, an ECG unit 2435 may be used, which optionally communicates with the device 100 or one or more other devices (e.g., the device 2430, 2440, etc.)

The system 2400 includes a device programmer 2430 having a wand unit 2431 for communicating with the implantable device 100. The programmer 2430 may further include communication circuitry for communication with another computing device 2440, which may be a server. The computing device 2440 may be configured to access one or more data stores 2450, for example, such as a database of information germane to a patient, an implantable device, therapies, etc.

The programmer 2430 and/or the computing device 2440 may include various information such as RV data 2010, LV data 2020 and modules (e.g., processor-executable instructions) for performing various actions of the methods 1800, 1900, 2100, 2200, etc., noting that a particular implementation of a method use more than one device.

The programmer 2430 optionally includes features of the commercially available 3510 programmer and/or the MERLIN™ programmer marketed by St. Jude Medical, Sylmar, Calif. The MERLIN™ programmer includes a processor, ECC (error-correction code) memory, a touch screen, an internal printer, I/O interfaces such as a USB that allows a device to connect to the internal printer and attachment of external peripherals such as flash drives, Ethernet, modem and WiFi network interfaces connected through a PCMCIA/ CardBus interface, and interfaces to ECG and RF (radio frequency) telemetry equipment.

The wand unit 2431 optionally includes features of commercially available wands. As shown, the wand unit 2431 attaches to a programmer 2430, which enables clinicians to conduct implantation testing and performance threshold testing, as well as programming and interrogation of pacemakers, implantable cardioverter defibrillators (ICDs), emerging indications devices, etc.

During implant, a system such as a pacing system analyzer (PSA) may be used to acquire information, for example, via one or more leads. A commercially available device marketed as WANDA™ (St. Jude Medical, Sylmar, Calif.) may be used in conjunction with a programmer such as the MERLIN™ programmer or other computing device (e.g., a device that includes a processor to operate according to firmware, software, etc.). Various exemplary techniques described herein may be implemented during implantation and/or after implantation of a device for delivery of electrical stimulation (e.g., leads and/or pulse generator) and the types of equipment for acquiring and/or analyzing information may be selected accordingly.

The wand unit 2431 and the programmer 2430 allow for display of atrial and ventricular electrograms simultaneously during a testing procedure. Relevant test measurements, along with customizable implant data, can be displayed, stored, and/or printed in a comprehensive summary report for the patient's medical records and physician review and/or for other purposes.

In the example of FIG. 24, the data store 2450 may include information such as measures and values, scores, etc. Such information may be used by a model, in making a comparison, in making a decision, in adjusting a therapy, etc. Such information may be updated periodically, for example, as the device 100 (or other device(s)) acquires new patient information. The computing device 2440 may use information stored in the data store 2450 to periodically update criteria such as thresholds for use in determining a score (see, e.g., the criteria presented above for the four parameter model). The system 2400 is an example as other equipment, instructions, etc., may be used or substituted for features shown in FIG. 24.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   detecting a QRS complex using cutaneous electrodes;
   during the QRS complex, detecting an R-wave of a ventricle using an intracardiac electrode;
   determining if the R-wave occurred during a first, predetermined percentage of the QRS complex width;
   based at least in part on the determining, assigning a value to an EGM/ECG parameter where the EGM/ECG parameter comprises a parameter of a score for assessing a patient's likelihood of responding to cardiac resynchronization therapy;
   sensing activity of the ventricle using at least the intracardiac electrode;
   sensing activity of the other ventricle using at least one different intracardiac electrode;
   determining an interval between activity of one ventricle and activity of the other ventricle wherein activation in one ventricle causes the activity in the other ventricle from either the right ventricle to the left ventricle or from the left ventricle to the right ventricle; and
   based at least in part on the determining, assigning a value to a IVCD parameter where the IVCD parameter comprises a parameter of a score for assessing the patient's likelihood of responding to cardiac resynchronization therapy.

2. The method of claim 1 wherein the intracardiac electrode comprises an epicardial electrode.

3. The method of claim 1 wherein the intracardiac electrode comprises an electrode positioned in a cardiac chamber.

4. The method of claim 1 wherein the intracardiac electrode comprises an electrode positioned in a venous structure.

5. The method of claim 1 wherein if the R-wave did not occur during the first, predetermined percentage of the QRS complex width, the assigning assigns a value, to the EGM/ECG parameter, unfavorable to a patient's likelihood of responding to cardiac resynchronization therapy.

6. The method of claim 1 wherein the first, predetermined percentage comprises approximately 50%.

7. The method of claim 1 wherein if the interval exceeds approximately 150 ms, the assigning assigns a value, to the IVCD parameter, unfavorable to the patient's likelihood of responding to cardiac resynchronization therapy.

8. The method of claim 1 wherein activation in the right ventricle causes the activity in the left ventricle and wherein the interval corresponds to an interventricular conduction delay from the right ventricle to the left ventricle and further comprising:
   delivering stimulation energy to the left ventricle and sensing activity of the right ventricle caused by the delivered stimulation energy to the left ventricle;
   determining an interval between activation of the left ventricle and activity of the right ventricle wherein the interval corresponds to an interventricular conduction delay from the left ventricle to the right ventricle;
   calculating a difference between the interventricular conduction delay from the right ventricle to the left ventricle (IVCD-RL) and the interventricular conduction delay from the left ventricle to the right ventricle (IVCD-LR); and
   based at least in part on the calculating, assigning a value to a ΔIVCD parameter where the ΔIVCD parameter comprises a parameter of a score for assessing the patient's likelihood of responding to cardiac resynchronization therapy.

9. The method of claim 8 wherein if the difference exceeds approximately 100 ms, the assigning assigns a value, to the ΔIVCD parameter, unfavorable to the patient's likelihood of responding to cardiac resynchronization therapy.

10. A method comprising:
    detecting a QRS complex using cutaneous electrodes;
    during the QRS complex, detecting an R-wave of a ventricle using an intracardiac electrode;
    determining if the R-wave occurred during a first, predetermined percentage of the QRS complex width;
    based at least in part on the determining, assigning a value to an EGM/ECG parameter where the EGM/ECG parameter comprises a parameter of a score for assessing a patient's likelihood of responding to cardiac resynchronization therapy;

sensing activity of the ventricle and sensing activity of the other ventricle;

determining an interval between activity of one ventricle and activity of the other ventricle; and based at least in part on the determining, assigning a value to a Δ parameter where the Δ parameter comprises a parameter of a score for assessing the patient's likelihood of responding to cardiac resynchronization therapy.

11. The method of claim 10 wherein if the absolute value of the interval exceeds approximately 80 ms, the assigning assigns a value, to the Δ parameter, unfavorable to the patient's likelihood of responding to cardiac resynchronization therapy.

* * * * *